United States Patent
Jones et al.

(10) Patent No.: US 11,526,947 B2
(45) Date of Patent: *Dec. 13, 2022

(54) COMPUTER-BASED SYSTEMS EMPLOYING A NETWORK OF SENSORS TO SUPPORT THE STORAGE AND/OR TRANSPORT OF VARIOUS GOODS AND METHODS OF USE THEREOF TO MANAGE LOSSES FROM QUALITY SHORTFALL

(71) Applicant: MUNICH RE, Munich (DE)

(72) Inventors: Richard B. Jones, Georgetown, TX (US); Stefan C. Froehlich, Moosinning (DE); Ronald Kargl, Munich (DE); Richard Walter Bridges, West Newbury, MA (US); Christoph Kalinski, Oxford, MD (US); Veenet Muthraja, Munich (DE)

(73) Assignee: MUNICH RE, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/809,760

(22) Filed: Mar. 5, 2020

(65) Prior Publication Data

US 2020/0202451 A1    Jun. 25, 2020

Related U.S. Application Data

(63) Continuation of application No. 16/158,697, filed on Oct. 12, 2018, now Pat. No. 10,621,674.

(Continued)

(51) Int. Cl.
  G06Q 40/08    (2012.01)
  H04W 4/38    (2018.01)
  G06Q 10/08    (2012.01)

(52) U.S. Cl.
  CPC .......... G06Q 40/08 (2013.01); G06Q 10/083 (2013.01); H04W 4/38 (2018.02)

(58) Field of Classification Search
  CPC .... G06Q 40/08; G06Q 10/0833; G06Q 50/30; G06Q 20/08; H04W 4/021; H04W 4/02; H04W 4/38; G08G 1/207; G01S 19/42
  See application file for complete search history.

(56) References Cited

U.S. PATENT DOCUMENTS 6,764,004 B2    7/2004    White
6,832,205 B1    12/2004    Aragones et al.
(Continued)

FOREIGN PATENT DOCUMENTS

AU    2008219433    10/2013
AU    2013276981    10/2013
(Continued)

OTHER PUBLICATIONS

Cargoinsurance.com "Cargo Insurance: Things to Know" <https://www.cargoinsurance.com/cargo-insurance/> (<http://web.archive.org/web/20160406080901/https://www.cargoinsurance.com/cargo-insurance/> captured on Apr. 6, 2016 using Wayback Machine). (Year: 2016).*

(Continued)

*Primary Examiner* — Jeff Zimmerman
*Assistant Examiner* — Brian A Tallman
(74) *Attorney, Agent, or Firm* — Greenberg Traurig LLP

(57) ABSTRACT

In some embodiments, the present disclosure provides a network of multi-functional sensors; where, based on a quality insurance, each multi-functional sensor is positioned in, on, or in a vicinity of: a transported cargo and/or a cargo container, containing the transported cargo; where each multi-functional sensor is configured to measure particular transport-related condition, particular cargo-related condi- (Continued)

tion, or both, to form cargo transport sensor data and wirelessly transmit it to a server that is configured to dynamically predict, based on the cargo transport sensor data, a predicted quality loss of the transported cargo, determine a current loss value of the transported cargo and cause one or more remedial actions that include instantaneously instructing to pay a payout amount to an owner of the transported cargo to compensate for the current loss value and/or transmitting a remedial instruction with an adjustment to the operation of one or more of a cargo transport, the cargo container, and a cargo storage.

22 Claims, 21 Drawing Sheets
(4 of 21 Drawing Sheet(s) Filed in Color)

Related U.S. Application Data

(60) Provisional application No. 62/571,975, filed on Oct. 13, 2017.

(56) References Cited

U.S. PATENT DOCUMENTS

| | | |
|---|---|---|
| 6,865,516 B1 | 3/2005 | Richardson |
| 6,982,640 B2 | 1/2006 | Lindsay et al. |
| 7,149,658 B2 | 12/2006 | Kadaba |
| 7,286,990 B1 | 10/2007 | Edmonds et al. |
| 7,339,469 B2 | 3/2008 | Braun |
| 7,455,225 B1 | 11/2008 | Hadfield et al. |
| 7,495,558 B2 | 2/2009 | Pope et al. |
| 7,693,608 B2 | 4/2010 | Nasle |
| 7,711,654 B2 | 5/2010 | Schmidtberg et al. |
| 7,729,808 B2 | 6/2010 | Nasle et al. |
| 7,840,395 B2 | 11/2010 | Nasle et al. |
| 8,022,832 B2 | 9/2011 | Vogt et al. |
| 8,195,484 B2 | 6/2012 | Jones et al. |
| 8,229,771 B1 | 7/2012 | Billman |
| 8,248,254 B2 | 8/2012 | Vogt et al. |
| 8,484,386 B2 | 7/2013 | Phan |
| 8,548,833 B2 | 10/2013 | Jones et al. |
| 8,554,588 B2 | 10/2013 | Jones et al. |
| 8,554,589 B2 | 10/2013 | Jones et al. |
| 8,595,036 B2 | 11/2013 | Jones et al. |
| 8,676,610 B2 | 3/2014 | Jones et al. |
| 8,719,059 B2 | 5/2014 | Jones et al. |
| 8,812,331 B2 | 8/2014 | Jones et al. |
| 8,959,036 B2 | 2/2015 | Huat |
| 8,989,053 B1 | 3/2015 | Skaaksrud et al. |
| 9,087,333 B2 | 7/2015 | Kim et al. |
| 9,280,681 B2 | 3/2016 | Gettings et al. |
| 9,368,007 B2 | 6/2016 | Vogt et al. |
| 9,501,920 B2 | 11/2016 | Harring et al. |
| 9,710,740 B2 | 7/2017 | Morimoto |
| 9,886,799 B2 | 2/2018 | Kwak |
| 9,965,939 B2 | 5/2018 | Blair et al. |
| 10,009,667 B2 | 6/2018 | Taylor |
| 10,621,674 B2 | 4/2020 | Jones |
| 2001/0018628 A1* | 8/2001 | Jenkins .................. G08G 1/202 701/33.4 |
| 2002/0163436 A1 | 11/2002 | Singh et al. |
| 2003/0115978 A1 | 6/2003 | Moehnke et al. |
| 2003/0171879 A1 | 9/2003 | Pittalwala et al. |
| 2004/0122625 A1 | 6/2004 | Nasser et al. |
| 2004/0226392 A1 | 11/2004 | McNally |
| 2006/0164239 A1 | 7/2006 | Loda |
| 2006/0277109 A1 | 12/2006 | Kerth et al. |
| 2007/0040647 A1 | 2/2007 | Saenz et al. |
| 2007/0056369 A1 | 3/2007 | Griffin et al. |
| 2007/0076779 A1 | 4/2007 | Haarer |
| 2007/0124020 A1 | 5/2007 | Staples |
| 2007/0267509 A1 | 11/2007 | Witty et al. |
| 2007/0285238 A1 | 12/2007 | Batra |
| 2008/0015827 A1 | 1/2008 | Tryon et al. |
| 2008/0052044 A1 | 2/2008 | Shoenfeld |
| 2008/0111674 A1 | 5/2008 | Quine |
| 2008/0129490 A1 | 6/2008 | Linville et al. |
| 2008/0197969 A1 | 8/2008 | Vogt et al. |
| 2008/0231438 A1 | 9/2008 | Curcio |
| 2008/0300888 A1 | 12/2008 | Dell'Anno et al. |
| 2008/0303897 A1 | 12/2008 | Twitchell, Jr. |
| 2009/0093996 A1 | 4/2009 | Fluegge et al. |
| 2009/0281929 A1 | 11/2009 | Boitet et al. |
| 2009/0322510 A1 | 12/2009 | Berger et al. |
| 2010/0152962 A1 | 6/2010 | Bennett et al. |
| 2010/0262442 A1 | 10/2010 | Wingenter |
| 2011/0029413 A1 | 2/2011 | Ben-Tzur et al. |
| 2012/0107191 A1 | 5/2012 | Strahle et al. |
| 2013/0173325 A1 | 7/2013 | Coleman |
| 2013/0262064 A1 | 10/2013 | Mazzaro et al. |
| 2013/0298575 A1 | 11/2013 | Stark et al. |
| 2014/0279574 A1 | 9/2014 | Gettings et al. |
| 2015/0039347 A1* | 2/2015 | Sharma .............. G06Q 10/0833 705/4 |
| 2015/0046361 A1* | 2/2015 | Williams ............. G06Q 10/083 705/330 |
| 2015/0177094 A1 | 6/2015 | Friedlander et al. |
| 2015/0254600 A1 | 9/2015 | Murthy et al. |
| 2015/0371182 A1 | 12/2015 | Lucas et al. |
| 2016/0063433 A1* | 3/2016 | Glasgow ............ G06Q 10/0832 705/332 |
| 2016/0110683 A1 | 4/2016 | Gupta et al. |
| 2016/0253880 A1 | 9/2016 | Vogt |
| 2016/0260058 A1 | 9/2016 | Benjamin et al. |
| 2016/0260059 A1 | 9/2016 | Benjamin et al. |
| 2017/0363479 A1 | 12/2017 | Harvey |
| 2018/0195869 A1* | 7/2018 | High .................. G01C 21/3453 |
| 2018/0247262 A1 | 8/2018 | Arena |
| 2019/0114714 A1 | 4/2019 | Jones |

FOREIGN PATENT DOCUMENTS

| | | | |
|---|---|---|---|
| CN | 101799898 | 8/2010 | |
| CN | 107255989 | 10/2017 | |
| CN | 107515578 | 12/2017 | |
| CN | 207407930 | 5/2018 | |
| DE | 102005003562 | 1/2007 | |
| EP | 2105688 | 9/2009 | |
| EP | 2394239 | 12/2011 | |
| EP | 1741074 | 3/2013 | |
| EP | 1741074 B1 * | 3/2013 | ......... G06K 19/0717 |
| EP | 2257875 | 1/2015 | |
| EP | 3118824 | 1/2017 | |
| IN | 2010CH03693 | 7/2012 | |
| KR | 2009045596 | 5/2009 | |
| KR | 2012121383 | 11/2012 | |
| KR | 20120121382 | 11/2012 | |
| NZ | 579400 | 12/2012 | |
| NZ | 616724 | 12/2015 | |
| WO | 2004/038626 | 5/2004 | |
| WO | WO-2004038626 A1 * | 5/2004 | ............. G06Q 10/10 |
| WO | 2004/107770 | 12/2004 | |
| WO | 2008/151438 | 12/2008 | |
| WO | 2009/095919 | 8/2009 | |
| WO | 2013/142896 | 10/2013 | |
| WO | 2014/146014 | 9/2014 | |
| WO | 2017/158879 | 9/2017 | |
| WO | 2019/075323 | 4/2019 | |

OTHER PUBLICATIONS

Lang et al., "The Intelligent Container—A Cognitive Sensor Network for Transport Management". Mar. 2011, IEEE Sensors Journal, vol. 11, No. 3. p. 688-698 (Year: 2011).*

Weidong Wang, A Remote Monitoring System of Logistics Carrier Based on Wireless Sensor Network, International Journal of Online Engineering, Jan. 15, 2018, vol. 14, No. 01 (2018).

Amrita Srivastava & Ankita Gulati, iTrack: IoT framework for Smart Food Monitoring System, International Journal of Computer Applications (0975-8887), Aug. 2016, vol. 148—No. 12.

(56) References Cited

OTHER PUBLICATIONS

Giuseppe Elia Biccario et al., Wireless Remote Environmental Monitoring and Control of Perishable Goods in Maritime Transportation, Jul. 2014, https://www.researchgate.net/publication/279922128.

Jung Rainer et al, "Potential wine ageing during transportation", BIO Web of Conferences, 37th World Congress of Vine and Wine and 12th General Assembly of the OIV, EDP Sciences, Mar. 2014.

United States Patent and Trademark Office; PCT International Search Report and Written Opinion, issued in connection to PCT/US2018/055603; dated Dec. 14, 2018; 17 pages; U.S.

Murat Dener et al.; Ensuring of Safe Transmport of Goods and Cargos and Monitoring of Vibration Levels Using Wireless Sensor Networks; International Journal of Advances in Science Engineering and Technology, ISSN 2324-9009; vol. 3, Issue-; Apr. 2015; 4 pages.

Reiner Jedermann et al.; Intelligent Containers and Sensor Networks Approaches to Apply Autonomous Cooperation on Systems with Limited Resources; 2 pages; 2007.

Fleet Locate by Spireon; Spireon Infroduces New FleetLocate Cargo Sensor with Breakthrough Intelliscan Sensing Technology; Jul. 9, 2018; 2 pages.

Farrugia, H. et al.; The Effect of Temperature Changes on the Quality of Pharmaceutical Products During International Transportation; University of Malta, Dept. of Pharmacy; 1 page; Malta.

Praeger, Ulrike et al.; Effect of Storage Climate on Green-Life Duration of Bananas; 5th International Workshop, Cold Chain Management; Jun. 2013; 7 pages; Germany.

Kader, A.A.; Banana: Recommendations for Maintaining Postharvest Quality, Banana Produce Fact Sheets; Univerity of California, Davis; Postharvest Technology Center; 2012; 4 pages.

Kerbel, E.; Banana and Plaintain; Agriculture Handbook No. 66; The Commercial Storage of Fruits, Vegetables and Florist and Nursery Stocks; 2004; 7 pages; United States Department of Agricultire.

Broughton, W.J. et al.; Storage Conditions and Ripening of Two Cultivars of Banana; Scientia Horticulturae, 10; pp. 83-93; 1979; The Netherlands.

Jung, Rainer et al.; Potential Wine Ageing During Transportation; Bio Web of Conferences 3, EDP Sciences; 2014; 6 pages.

\* cited by examiner

CARGO AND QUALITY METRICS DATABASE FIELDS

| Source | Destination | Data Shipped | Date Arrived | Shipper Code | Container Type | Shipment Value (USD) | Salvage Value (USD) | Quality Metric |
|---|---|---|---|---|---|---|---|---|
| Argentina | Belgium | 01/20/15 | 02/28/15 | 9014 | 10 ft Dry | 621,000 | 186,300 | 62 |
| Spain | Poland | 11/08/15 | 11/26/15 | 9071 | 40 ft Dry | 698,000 | 69,800 | 75 |
| New Zealand | Taiwan (Province of China) | 12/22/15 | 01/10/16 | 9094 | 20 ft Dry | 299,000 | 119,600 | 83 |
| Italy | Seychelles | 10/18/15 | 11/21/15 | 9026 | Reefer | 631,000 | 0 | 83 |
| Germany | Lebanon | 08/29/15 | 10/03/15 | 9064 | Reefer | 581,000 | 290,500 | 92 |
| South Africa | Australia | 03/13/15 | 03/30/15 | 9014 | Thermal | 755,000 | 226,500 | 55 |
| Australia | Taiwan (Province of China) | 08/20/15 | 09/11/15 | 9053 | 10 ft Dry | 437,000 | 218,500 | 82 |
| Switzerland | Guadeloupe | 02/21/15 | 04/11/15 | 9099 | Thermal | 327,000 | 65,400 | 75 |
| Argentina | United Kingdom | 07/04/15 | 08/16/15 | 9086 | 20 ft Dry | 738,000 | 0 | 98 |
| Switzerland | Macao | 09/01/15 | 09/24/15 | 9067 | 20 ft Dry | 619,000 | 61,900 | 72 |
| Australia | Germany | 09/19/15 | 10/24/15 | 9083 | 40 ft Dry | 700,000 | 210,000 | 63 |
| Australia | France | 12/26/15 | 01/21/16 | 9047 | 40 ft Dry | 653,000 | 0 | 91 |
| France | Russian Federation | 08/03/15 | 09/13/15 | 9085 | 20 ft Dry | 620,000 | 248,000 | 93 |
| Australia | Saint Barthelemy | 12/23/15 | 02/21/16 | 9004 | Reefer | 768,000 | 76,800 | 62 |
| Argentina | Spain | 07/12/15 | 08/22/15 | 9017 | 40 ft Dry | 252,000 | 0 | 92 |
| Germany | Austria | 02/27/15 | 03/29/15 | 9050 | 10 ft Dry | 692,000 | 69,200 | 72 |
| South Africa | Norway | 01/24/15 | 02/23/15 | 9055 | Thermal | 611,000 | 305,500 | 85 |
| Argentina | Russian Federation | 02/14/15 | 03/04/15 | 9049 | Reefer | 524,000 | 104,800 | 53 |
| Spain | Argentina | 04/17/15 | 05/11/15 | 9004 | Thermal | 267,000 | 80,100 | 62 |
| United Kingdom | Germany | 07/31/15 | 09/22/15 | 9028 | Reefer | 550,000 | 220,000 | 60 |
| New Zealand | Argentina | 01/29/15 | 02/22/15 | 9026 | 10 ft Dry | 613,000 | 122,600 | 68 |
| France | United Kingdom | 06/12/15 | 07/22/15 | 9068 | 20 ft Dry | 439,000 | 0 | 78 |
| South Africa | Liechtenstein | 02/02/15 | 03/31/15 | 9028 | Thermal | 732,000 | 146,400 | 75 |
| Italy | Luxembourg | 05/28/15 | 06/20/15 | 9038 | 40 ft Dry | 686,000 | 274,400 | 84 |
| France | Netherlands | 12/08/15 | 12/29/15 | 9080 | 40 ft Dry | 340,000 | 0 | 64 |
| ............ | ............ | ............ | ............ | ............ | ............ | ............ | ............ | ............ |
| ............ | ............ | ............ | ............ | ............ | ............ | ............ | ............ | ............ |

FIG. 4

SAMPLE QUALITY SHORTFALL MODEL DATA WITH SHIPMENT DATA

FIG. 7

| Travel/Storage Temperature Range | Average Actual Travel Temperature Range | | $P_{95}$ Actual Travel Temperature | |
|---|---|---|---|---|
| | Green ( 0 - 4°C ) | 2100 Sensor Data Result | Green ( > 7°C ) | 2140 Sensor Data Result |
| | Yellow ( >4 - 9 °C ) | | Yellow ( >7 - 12°C ) | |
| | Red ( < 0°C or > 9 °C ) | | Red ( > 12 °C ) | |
| Relative humidity | Green | Yellow | Red | Actual Relative Humidity |
| | 75% - 80% ( -1 - +1°C ) | 60% - 74% ( -1 - +1°C ) | <60% ( -1 - +1°C ) | 2150 Sensor Data Result |
| | 70% ( 8 - 10°C ) | 50% - 69% ( 8 - 10°C ) | <50% ( 8 - 10°C ) | |
| | 65% at 15°C | 50% - 64% at 15°C | <50% at 15°C | |
| Water content | Average Actual Water Content | | Shipment #: | Entered Before Transit |
| | Green (82% - 86%) | 2110 Sensor Data Result | Shipper: | Entered Before Transit |
| | Yellow (60% - 81%) | | Cargo Origin: | Entered Before Transit |
| | Red <60% or > 86% | | Cargo Destination: | Entered Before Transit |
| Maximum Equilibrium Moisture Content | Actual Max Equilibrium Moisture Content/Content | | | 2160 |
| | | | Start Date: | Entered Before Transit |
| | Green: 60% - 65% | 2120 Sensor Data Result | Termination Date: | Entered After Transit |
| | Yellow: (30% - 59%) | | Insured Shipment Value: | Entered Before Transit |
| | Red: <30% or > 65% | | | |
| Ventilation | Actual Average Ventilation (circulations/hour) | | Journey Quality | Insurance Claim Payment |
| | Green: 60 - 80 | 2130 Sensor Data Result | All Green | 0$ 2170 |
| | Yellow: 30 - 59 | | >1 Yellow and No Reds | X% of Insured Value - Deductible |
| | Red: < 30 | | # of Reds >0 | Y% of Insured Value - Deductible |

FIG. 21

Wine Category Quality Measurement Criteria

| Looks - Color (max. 5 pts.) | | % Remaining Value | Smell (max. 5 pts.) | | % Remaining Value | Taste (max. 5 pts.) | | % Remaining Value |
|---|---|---|---|---|---|---|---|---|
| 5 | Brilliant & Clear | 100% | 5 | Clear fruit definition & significant bouquet | 100% | 5 | Outstanding balance | 100% |
| 4 | Slightly cloudy | 95% | 4 | Some fruit definition & significant bouquet | 95% | 4 | Flavor: Good beginning - good ending | 95% |
| 3 | Moderately cloudy | 85% | 3 | Some fruit definition & some bouquet | 85% | 3 | Flavor: Good beginning good ending or vice versa | 85% |
| 2 | Off color but clear | 85% | 2 | Little fruit definition & some bouquet | 85% | 2 | Acidity balance | 75% |
| 1 | Off color and cloudy | 75% | 1 | Little fruit definition & little bouquet | 75% | 1 | Poor Palate Texture | 85% |
| 0 | Awful | 85% | 0 | Awful | 5% | 0 | Awful | 25% |

FIG. 22

COMPUTER-BASED SYSTEMS EMPLOYING A NETWORK OF SENSORS TO SUPPORT THE STORAGE AND/OR TRANSPORT OF VARIOUS GOODS AND METHODS OF USE THEREOF TO MANAGE LOSSES FROM QUALITY SHORTFALL

CROSS-REFERENCE TO RELATED APPLICATIONS

The present application claims priority from U.S. Provisional Patent Application No. Provisional Appl. No. 62/571,975, entitled "COMPUTER-BASED SYSTEMS EMPLOYING A NETWORK OF SENSORS TO SUPPORT THE TRANSPORT OF VARIOUS GOODS AND METHODS OF USE THEREOF TO MANAGE LOSSES FROM QUALITY SHORTFALL DURING THE TRANSPORT," and filed Oct. 13, 2017, and is a continuation of U.S. patent application Ser. No. 16/158,697, entitled "COMPUTER-BASED SYSTEMS EMPLOYING A NETWORK OF SENSORS TO SUPPORT THE STORAGE AND/OR TRANSPORT OF VARIOUS GOODS AND METHODS OF USE THEREOF TO MANAGE LOSSES FROM QUALITY SHORTFALL," and filed Oct. 12, 2018, both of which are incorporated herein by reference in their entirety for all purposes.

BACKGROUND OF THE INVENTION

On occasion, cargo storage and/or transport may result in property loss from numerous perils such as, without limitation, perils related to weather, thief, mishandling, environmental stresses, equipment malfunction, fire, and/or any other potential quality-affecting event(s). For example, transporting cargo is a highly complex and nontransparent industry with many isolated processes for each stakeholder in the value chain. For example, there are numerous technological problems that have been associated with transporting and storing the cargo, such as but not limited to perishable goods, antiques, pharmaceuticals, automobile parts, computer parts, etc. As detailed herein, in at least some of embodiments, the term cargo transport and its derivatives includes all activities (including in-transit storage, etc.) and all parties from a time the cargo leaves a manufacturer's site and/or seller's site to a delivery place as identified, for example, in cargo transport documents. As detailed herein, while may embodiments herein have been described with respect the cargo transport, a person skilled in the art that the present disclosure may be equally applicable as technological solution(s) to manage losses due to quality shortfall during the storage (e.g., storing meats in a meat locker (refrigerator) at a restaurant).

One technological problem is limited ability to predict when equipment (e.g., ship's engine, etc.) involved the cargo transport might fail or to monitor and/or modify environmental conditions such as refrigeration. For example, a technological solution is wanted to predict prior to and/or during the cargo transport that a cargo transporter (e.g., truck, ship, plane) and/or cargo containers (e.g., refrigerated containers/reefers, etc.) might experience an equipment failure during transport that would negatively impact the quality of the cargo so that one or more remedial actions might be implemented in real-time to reduce and/or eliminate such negative impact.

Another technological problem, that might also be related to the technological problem identified above, is that typically the cargo transport travels along routes that have no or severely diminished computer and/or communication infrastructure (e.g., open sea, desert, Canadian's Boreal forest, etc.) so that even if the cargo transport and/or cargo container is/are retrofitted with some type of environmental and/or operational sensor(s), transmitting sensor data and/or equipment operational data (e.g., telematic data) in real-time to a transport command center and/or taking real-time remedial action(s) to reduce and/or eliminate such negative impact to the quality of the cargo may be negatively impacted due to the diminished computing and/or communication infrastructure and/or technical limitations of equipment (e.g., sensors requiring sufficient power for long distance transmission of the sensor/operational data).

Another technical problem is recording the specific time when a loss and/or damage may have occurred. With multiple parties involved in storing and/or transporting goods, it can be difficult to assign liability to the proper party. For example, a shipment from China to the United States that moves via ocean container may have a consolidation warehouse and multiple trucks or rail carriers involved in China before arrival at the port and then once in the United States, a deconsolidation warehouse and multiple trucks or rail carriers before arriving at the intended destination. A technological solution is to have a third party (for example, without limitation, a sensor-managing entity) record/determine when the loss occurred to properly assign liability to the party that may have caused the damage. This then allows the cargo owner or their insurance company to verifiably seek compensation and/or subrogate against that party.

Yet another technological problem is how to timely process and generate electronic remedial instruction(s) that affect(s) or is/are designed to affect, for example, in real-time, the cargo transport (e.g., vehicle, ship, plane, etc.), cargo storage (e.g., refrigerated container, etc.), or both, in a positive feedback loop to reduce or eliminate the quality shortfall of the goods (e.g., perishable goods, antiques, auto parts, etc.). For example, on one hand, the environmental and/or operational sensor data, as detailed herein, typically might be collected/generated by one type of equipment (e.g., data-collecting sensors), whereas electronic remedial instruction(s), and thus communication link(s) must be typically established with another type of equipment (e.g., truck's electronic computer unit (ECU)) to affect how the transport (e.g., vehicle, ship, airplane, etc.), cargo storage (e.g., refrigerated container, etc.), or both behave/operate.

Yet another technological problem is that a typical, conventional computational hardware (e.g., servers) and a typical, conventional networking/transmission hardware (e.g., routers, re-transmitters, antennas, etc.) are unable to adjust their operational capabilities based, for example without limitation, a type of remedial action and/or a type of transport equipment being involved.

Yet another technological problem is that a typical, conventional computational hardware (e.g., servers) might not allow all stakeholders in the cargo transport and/or storage industries to transparently access and/or reliably verify transport and/or storage data that provides a wholesome view in numerous, if not all, aspects of the cargo transport.

Another technological problem is that a typical, conventional cargo insurance claims are not started until a loss adjuster or claims surveyor has viewed the damage to the merchandise (e.g., at the end destination in the case of the cargo transport, or the surveyor found an availability (maybe in a few days or a week) to visit the restaurant to view the spoiled meat). For example, cargo transits can take over a month in the case of ocean transport. A technological solution is to create parameters from the sensor derived data to determine when perils related to weather, thief, mishandling, environmental stresses, equipment malfunction, fire, and/or any other potential quality-affecting event(s) may have occurred and allowing an insurance company to begin and or even finalize the claim process (i.e., pay out the compensation) while the goods are still in transit (e.g., allowing the sender to send a new shipment when, based on the sensor derive data, the sender receives a compensation).

Another technological problem is that the typical cargo storage and transport insurance underwriting process relies on anecdotal information to determine policy terms and price. A technological solution is to use historical sensor-based and/or sensor-collected transit and storage data to automatically and dynamically manage the cargo storage and/or cargo transport insurance process lifecycles, from underwriting to claim adjudication.

BRIEF SUMMARY OF THE INVENTION

In some embodiments and, optionally, in combination of any embodiment described above or below, the at least some embodiments of the present disclosure utilize a network of multi-functional sensors of various types and related technologies to minimize and/or recoup quality shortfall (inherent vice) of cargo (land, marine, and air), especially environmentally sensitive cargos. For example, medical drug and many foods shipments require very specific temperature and humidity ranges. In some embodiments and, optionally, in combination of any embodiment described above or below, the at least some embodiments of the present disclosure transform sensory data, such as, without limitation, a time series of, for example, temperature and humidity readings into inventive metric(s) of the present disclosure that can be used to mitigate and/or recoup quality shortfall of cargo. In some embodiments and, optionally, in combination of any embodiment described above or below, the inventive systems and methods of the present disclosure may utilize various inputs such as, without limitation, various scoring approaches to obtain the inventive metric(s).

In some embodiments and, optionally, in combination of any embodiment described above or below, the at least some embodiments of the present disclosure utilize a network of multi-functional sensors; where, based at least in part on a quality insurance, each multi-functional sensor of the network of sensors is positioned in, positioned on, or positioned in a vicinity of at least one of: i) a transported cargo, where the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, ii) wirelessly transmit, via one or more communication modes, the cargo transport sensor data from the respective sensor to at least one server, iii) wirelessly receive, from the at least one server, via the one or more communication modes, one or more remedial instructions and store the one or more remedial instructions in a second memory location of the respective multi-functional sensor, and iv) cause the one or more remedial instructions to be implemented with one or more of: the at least one cargo container, the at least one cargo transport, and the at least one cargo storage; the at least one server, having cargo quality shortfall administration software stored on a non-transient computer readable medium; where the at least one server what is remotely located from the network of multi-functional sensors; where, upon execution of the cargo quality shortfall administration software, the at least one server is at least configured to: i) receive the cargo transport sensor data from the network of multi-functional sensors; ii) dynamically predict, based at least in part on the cargo transport sensor data, at least one current quality metric of the transported cargo, where the at least one current quality metric is representative of a predicted quality loss of the transported cargo from an original condition of the transported cargo at the at least one first geographic location; iii) dynamically determine, based at least in part on the at least one current quality metric of the transported cargo and a cargo-specific value remaining curve of the quality insurance, a current loss value of the transported cargo; iv) dynamically determine, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality insurance, a payout amount to an owner of the transported cargo to compensate the current loss value of the transported cargo without a physical inspection of the transported cargo, and 2) transmitting the one or more remedial instructions to one or more multi-functional sensors of the network of multi-functional sensors, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least some embodiments of the present disclosure provides a method, including at least the following steps of: installing a network of multi-functional sensors; where, based at least in part on a quality insurance, each multi-functional sensor of the network of sensors is positioned in, positioned on, or positioned in a vicinity of at least one of: i) a transported cargo, where the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, ii) wirelessly transmit, via one or more communication modes, the cargo transport sensor data from the respective sensor to at least one server, iii) wirelessly receive, from the at least one server, via the one or more communication modes, one or more remedial instructions and store the one or more remedial instructions in a second memory location of the respective multi-functional sensor, and iv) cause the one or more remedial instructions to be implemented with one or more of: the at least one cargo container, the at least one cargo transport, and the at least one cargo storage; receiving, by the at least one server, the cargo transport sensor data from the network of multi-functional sensors; where the at least one server is configured to execute cargo quality shortfall administration software stored on a non-transient computer readable medium associated with the at least one server; dynamically predicting, by the at least one server, based at least in part on the cargo transport sensor data, at least one current quality metric of the transported cargo, where the at least one current quality metric is representative of a predicted quality loss of the transported cargo from an original condition of the transported cargo at the at least one first geographic location; dynamically determining, by the at least one server, based at least in part on the at least one current quality metric of the transported cargo and a cargo-specific value remaining curve of the quality insurance, a current loss value of the transported cargo; dynamically determining, by the at least one server, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality insurance, a payout amount to an owner of the transported cargo to compensate the current loss value of the transported cargo without a physical inspection of the transported cargo, and 2) transmitting the one or more remedial instructions to one or more multi-functional sensors of the network of multi-functional sensors, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least some embodiments of the present disclosure utilize a network of multi-functional sensors; where, based at least in part on a quality determination, each multi-functional sensor of the network of sensors is positioned in, positioned on, or positioned in a vicinity of at least one of: i) a transported cargo, where the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, ii) wirelessly transmit, via one or more communication modes, and the cargo transport sensor data from the respective sensor to at least one server; the at least one server, having cargo quality shortfall administration software stored on a non-transient computer readable medium; where the at least one server what is remotely located from the network of multi-functional sensors; where, upon execution of the cargo quality shortfall administration software, the at least one server is at least configured to: i) receive the cargo transport sensor data from the network of multi-functional sensors; ii) dynamically predict, based at least in part on the cargo transport sensor data, at least one current quality metric of the transported cargo, where the at least one current quality metric is representative of a predicted quality loss of the transported cargo from an original condition of the transported cargo at the at least one first geographic location; iii) dynamically determine, based at least in part on the at least one current quality metric of the transported cargo and a cargo-specific value remaining curve of the quality determination, a current loss value of the transported cargo; iv) dynamically determine, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality determination, a payout amount to an owner of the transported cargo to compensate the current loss value of the transported cargo without a physical inspection of the transported cargo, and 2) transmitting the one or more remedial instructions, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least some embodiments of the present disclosure provides a method, including at least the following steps of: installing a network of multi-functional sensors; where, based at least in part on a quality determination, each multi-functional sensor of the network of sensors is positioned in, positioned on, or positioned in a vicinity of at least one of: i) a transported cargo, wherein the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, and ii) wirelessly transmit, via one or more communication modes, the cargo transport sensor data from the respective sensor to at least one server; receiving, by the at least one server, the cargo transport sensor data from the network of multi-functional sensors; where the at least one server is configured to execute cargo quality shortfall administration software stored on a non-transient computer readable medium associated with the at least one server; dynamically predicting, by the at least one server, based at least in part on the cargo transport sensor data, at least one current quality metric of the transported cargo, where the at least one current quality metric is representative of a predicted quality loss of the transported cargo from an original condition of the transported cargo at the at least one first geographic location; dynamically determining, by the at least one server, based at least in part on the at least one current quality metric of the transported cargo and a cargo-specific value remaining curve of the quality determination, a current loss value of the transported cargo; dynamically determining, by the at least one server, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality determination, a payout amount to an owner of the transported cargo to compensate the current loss value of the transported cargo without a physical inspection of the transported cargo, and 2) transmitting the one or more remedial instructions, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least one environmental condition is one of: temperature, humidity, vibration, shock, sound, light, presence of air contaminant, pH, location, presence of at least one odor, presence of at least one gas, physical integrity of one of the transported item or the plurality of transported items, and any combination thereof. For example, the gas sensors may measure one or more of ethylene, ammonia, acetylene, nitrogen, carbon dioxide, oxygen.

In some embodiments and, optionally, in combination of any embodiment described above or below, the at least one computer network communication is selected from the group consisting of electronic communications such as but limited to: NFC, RFID, Narrow Band Internet of Things (NBIOT), ZigBee, 3G, 4G, 5G, GSM, GPRS, WiFi, WiMax, CDMA, satellite and any combination thereof.

In some embodiments and, optionally, in combination of any embodiment described above or below, the at least one adjustment is a change in one or more operational parameters of one or more of: the at least one cargo transport, the at least one cargo container, and the at least one cargo.

In some embodiments and, optionally, in combination of any embodiment described above or below, the at least one adjustment is an instruction to replace one or more of: a current cargo transport, a current cargo container, and a current cargo storage, with one or more of: a new cargo transport, a new cargo container, and a new cargo storage, respectively.

In some embodiments and, optionally, in combination of any embodiment described above or below, the one or more operational parameters of the at least one cargo transport comprise a speed of the at least one cargo transport and wherein the at least one adjustment is a change in the speed of the at least one cargo transport.

In some embodiments and, optionally, in combination of any embodiment described above or below, the one or more operational parameters of the at least one cargo transport comprise a geographic direction of the at least one cargo transport and wherein the at least one adjustment is a change in the geographic direction of the at least one cargo transport.

In some embodiments and, optionally, in combination of any embodiment described above or below, the at least one server and the network of multi-functional sensors are associated with distinct entities.

In some embodiments and, optionally, in combination of any embodiment described above or below, the executing at least one remedial activity includes generating, in real-time, at least one alert configured to invoke at least one corrective action from the at least one transport.

In some embodiments and, optionally, in combination of any embodiment described above or below, the at least one corrective action is an instruction to change at least one transporting parameter.

In some embodiments and, optionally, in combination of any embodiment described above or below, where the at least one transporting parameter is an operational parameter of the at least one transport.

In some embodiments and, optionally, in combination of any embodiment described above or below, the at least one transporting parameter is a change in a transporting direction.

In some embodiments and, optionally, in combination of any embodiment described above or below, the at least one server having cargo quality shortfall administration software includes at least one machine learning algorithm configured to determine at least one of: i) the at least one current quality metric and ii) the at least one target quality metric.

In some embodiments and, optionally, in combination of any embodiment described above or below, the at least one machine learning algorithm is neural network.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows a sample of the type of data utilized in accordance with at least some embodiments of the present disclosure.

FIG. 7 shows a snapshot of a graphical user interface programmed to demonstrate an illustrative model how data is compiled and integrated in accordance with at least some embodiments of the present disclosure.

FIG. 9 shows a process flow in accordance with at least some embodiments of the present disclosure.

FIG. 10 shows another process flow in accordance with at least some embodiments of the present disclosure.

FIGS. 11-22 show exemplary graphs illustrating certain aspects of at least some embodiments of the present disclosure.

DETAILED DESCRIPTION OF THE INVENTION

The following disclosure provides many different embodiments, or examples, for implementing different features of a system and method for accessing and managing structured content. Specific examples of components, processes, and implementations are described to help clarify the invention. These are merely examples and are not intended to limit the invention from that described in the claims. Well-known elements are presented without detailed description so as not to obscure the preferred embodiments of the present disclosure with unnecessary detail. For the most part, details unnecessary to obtain a complete understanding of the preferred embodiments of the present disclosure have been omitted in as much as such details are within the skills of persons of ordinary skill in the relevant art.

Figure 1:
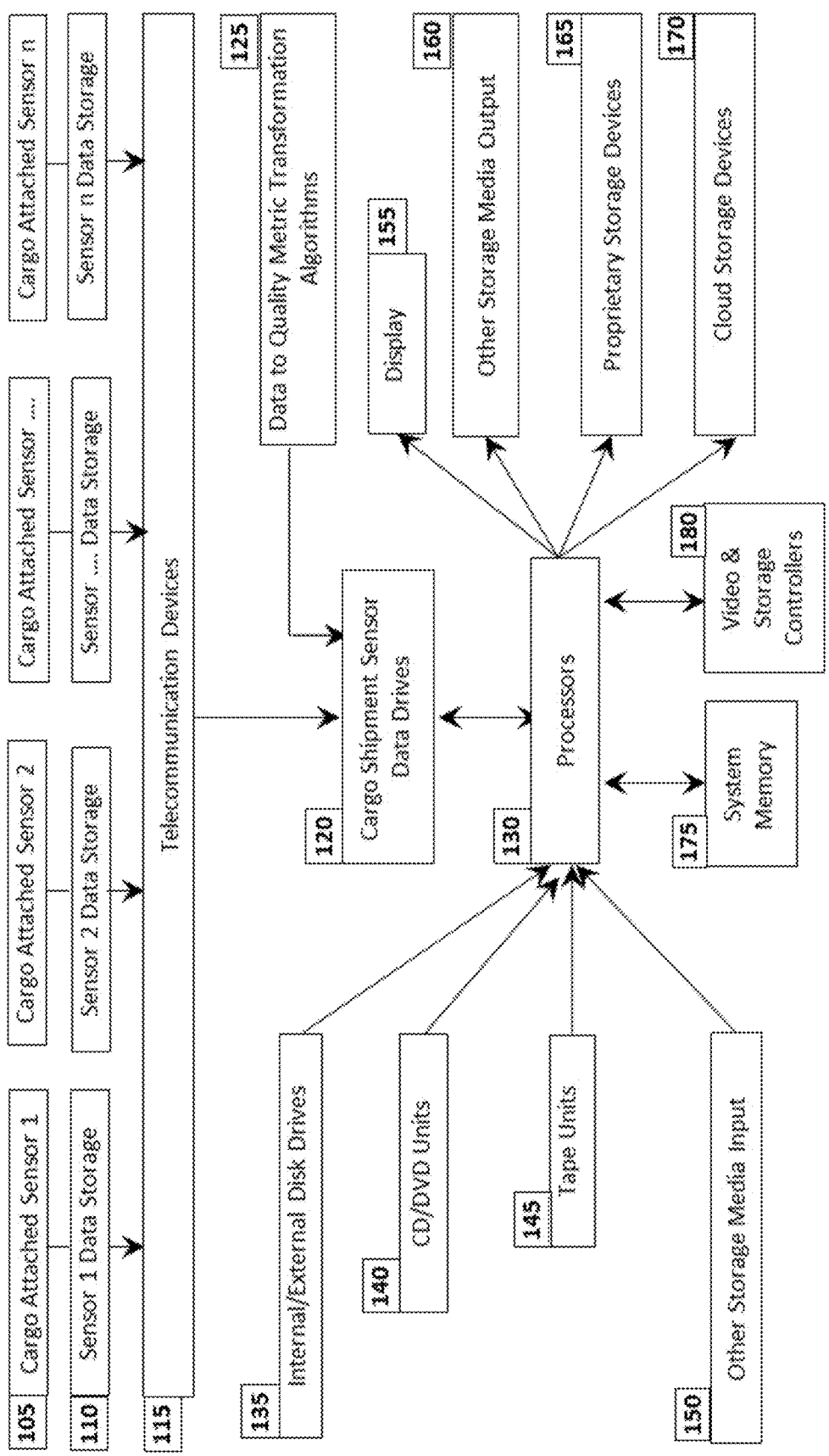
FIG. 1 is illustrative of computer-based system architecture for implementing a method of the invention.

FIG. 1 shows and exemplary architecture of an exemplary inventive computer-based system of the at least some embodiments of the present disclosure. In some embodiments and, optionally, in combination of any embodiment described above or below, the exemplary inventive computer-based system may be configured to include hardware components such as, without limitation, a collection of environmental condition and/or goods-related condition sensors 105, internal sensor data storage 110, telecommunication devices 115 and one or more processors 120 to perform the details of the premium calculations. In some embodiments, the telecommunication devices transmit the remote sensor data to central data storage medium 120. In some embodiments, additional hardware-based devices may be connected to the central storage medium to enable the data to be processed via 130 to compute quality metrics from the environmental data and then stored in the central storage medium. In some embodiments, the processors 130 execute a computer program residing in system memory 175 to perform the method. In some embodiments, video and storage controllers 180 may be used to enable the operation of display 155. In some embodiments, the exemplary system of the present disclosure may include various data storage devices for data input such as internal/external disk drives 135, internal CD/DVDs 140, tape units 145, and other types of electronic storage media 150. The aforementioned data storage devices are illustrative and exemplary only. These storage media are used to enter underwriting data, such as shipment values and quality metric to economic value relationships. The calculations can apply statistical software packages or can be performed from the data entered in spreadsheet formats using Microsoft Excel, for example. The calculations are performed using either customized software programs designed for company-specific system implementations or by using commercially available software that is compatible with Excel or other database and spreadsheet programs. In some embodiments, the exemplary system of the present disclosure can also interface with proprietary or public external storage media 165 to link with other databases to provide additional risk information such as weather data to the cargo transport underwriters. The output devices can be a telecommunication device 170 to transmit the calculation worksheets and other system produced graphs and reports via cloud storage devices 170, proprietary storage devices 165, other output media 160 such 140, 145, and 150. These output devices used herein are illustrative and exemplary only.

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" means that events and/or actions can be triggered and/or occur without any human intervention. In some embodiments and, optionally, in combination of any embodiment described above or below, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments and, optionally, in combination of any embodiment described above or below, the inventive specially programmed computing systems with associated devices (e.g., a network of remote sensors) are configured to operate in the distributed network environment, communicating over a suitable data communication network (e.g., the Internet, etc.) and utilizing at least one suitable data communication protocol (e.g., IPX/SPX, X.25, AX.25, AppleTalk™, TCP/IP (e.g., HTTP), etc.). Of note, the embodiments described herein may, of course, be implemented using any appropriate hardware and/or computing software languages. In this regard, those of ordinary skill in the art are well versed in the type of computer hardware that may be used, the type of computer programming techniques that may be used (e.g., object oriented programming), and the type of computer programming languages that may be used (e.g., C++, Objective-C, Swift, Java, JavaScript). The aforementioned examples are, of course, illustrative and not restrictive.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

In another form, a non-transitory article, such as a non-transitory computer readable medium, may be used with any of the examples mentioned above or other examples except that it does not include a transitory signal per se. It does include those elements other than a signal per se that may hold data temporarily in a "transitory" fashion such as RAM and so forth. In some embodiments and, optionally, in combination of any embodiment described above or below, the at least some embodiments of the present disclosure may rely on one or more distributes and/or centralized databases (e.g., data center).

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments and, optionally, in combination of any embodiment described above or below, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor.

Figure 2A:
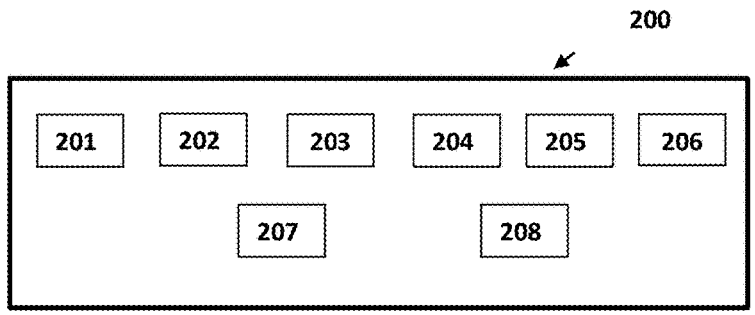
FIGS. 2A and 2B are block diagrams of exemplary sensor(s) utilized in accordance with some embodiments of the present disclosure.

In some embodiments and, optionally, in combination of any embodiment described above or below, exemplary sensors(s) of the present disclosure may sense and record at least environmental attributes such as, but not limited to, temperature, humidity, oxygen level, light, color, vibration, shock, acceleration, gyroscope data (orientation), air pressure, odors, gases (e.g. volatile organic compounds (VOC), nitrogen, ozone, $CO_2$), particular matters, pH, and any combination thereof. For example, as shown in FIG. 2A, an exemplary sensor unit of the present disclosure (200) may include one or more of: a temperature measuring sensor module (201) (e.g., DHT11 by Adafruit (NY, NY)), humidity measuring sensor module (202) (e.g., DHT11 by Adafruit (NY, NY)), shock measuring sensor module (203), acceleration measuring sensor module (204), gyroscope module (205), air pressure measuring sensor module (206), air quality measuring sensor module (e.g., particulate monitoring)(e.g., MQ13 by Adafruit (NY, NY)), magnetic sensor module (e.g., DRV5023 Digital-Switch Hall Effect Sensor, Texas Instruments Inc., Dallas, Tex.), and/or other suitable sensor modules. The exemplary sensor unit of the present disclosure may also include a control board (not shown) configured to allow communication exchange between one or more of the sensor modules and one or more microprocessors (207), programmed to operate the sensor modules. The exemplary sensor unit of the present disclosure may also include a battery (not shown). The exemplary sensor unit of the present disclosure may also include data memory storage (208) (e.g., an SD card).

In some embodiments, the exemplary sensor unit of the present disclosures may also include capturing optical parameter(s) that may include at least one from a group consisting of infrared, visible, and ultraviolet light parameters (e.g., TSL2561 by Adafruit (NY, NY)). For example, without limitation, the optical detection module may include a photo sensor to detect a level or change in level of light. In some embodiments, the optical detection may include a digital image capture device, such as, without limitation, a CCD or CMOS imager that captures data related to infrared, visible, and/or ultraviolet light images. For example, an exemplary light sensor can generate an indication of increased ambient light that may indicate the opening of a door that should not be open.

In some embodiments, the exemplary sensor unit of the present disclosure may also include an acoustic detection module capturing sound parameter(s) (e.g., sound levels, sound frequencies, etc.) (e.g., HC-SR04 by Adafruit (NY, NY)).

In some embodiments, the exemplary sensor unit of the present disclosure may also include a motion detection module capturing movement of the cargo and/or around the cargo.

The at least some embodiments of the present disclosure may utilize distinct sensors to separately capture environmental sensor data about the cargo's environment condition(s), cargo physical condition data about the cargo's physical condition(s), and transport equipment data about operational (e.g., power consumption, water consumption, etc.) and/or environmental condition(s) of the involved cargo transport equipment (e.g., ship, container, etc.).

The at least some embodiments of the present disclosure may utilize sensors that may be an active or real-time type of sensors that collect, store and forward their data in real time on a set interval or on an exception basis. In some embodiments, the active sensors of the present disclosure are connected to a data transmission unit (wired or wireless) to transmit and/or receive data.

The at least some embodiments of the present disclosure may utilize sensors that may be a passive type of sensors that collect and store their data without real-time transmission. In some embodiments, the passive sensors of the present disclosure need to be read (wired or wireless) manually or automatically, but are not connected to a data transmission unit.

Unless specifically called out, it is understood that the terms "sensor" and "sensors" as used herein can cover both types of sensors: the active and the passive sensors. In some embodiments, the exemplary sensors of the present disclosure can have one or more functions of sensors/monitors produced by at least one of the following companies:
1. Sensitech Inc. (Beverly Mass.),
2. DeltaTrak Inc. (Pleasanton, Calif.),
3. Elpro-Buchs AG (Switzerland),
4. Ellab A/S (Hillerod, Denmark),
5. Euroscan GmbH (Bonn, Germany),
6. Orbcomm Inc. (Rochelle Park, N.J.),
7. Coretex Limited (San Diego, Calif.),
8. Carrier eSolutions of Carrier Corp. (Syracuse, N.Y.),
9. ThermoKing (Minneapolis, Minn.), or
10. Roambee Corp. (Santa Clara, Calif.).

For example, in some embodiments, the exemplary sensor unit of the present disclosure (200) may include, without limitation, Chipcon's System On Chip (SOC) chip (e.g., CC2530, Texas Instruments, Inc.), one or more sensor modules, and power management module. For example, the power supply module may provide stable 3.3V voltage for the sensor modules through the voltage regulator. For example, each sensor module may transfer the sensor data through one or more general-purpose input/output (GPIO) port of the processor. For example, wireless sensor network wireless communication technology can use ZigBee protocol (short-range, low complexity, low power consumption, low data rate, low-cost two-way wireless communication technology or wireless network technology), Bluetooth, Wi-Fi and infrared and other technologies. For example, in some embodiments, the exemplary sensor unit of the present disclosure (200) may be configured to first convert, for example, humidity and/or temperature measurements into electrical signals, respectively, by, for example, a capacitive polymer humidity sensor and a temperature sensitive element made of energy gap material. For example, in some embodiments, the exemplary sensor unit of the present disclosure (200) may be configured to direct the electrical signal into the weak signal amplifier for amplification. Next, the electrical signal enters a 14-bit A/D converter. For example, in some embodiments, the exemplary sensor unit of the present disclosure (200) may be configured to output the digital signal through the two-wire serial digital interface. For example, to determine whether the goods in the carriage are safe, to judge whether the door is open, whether someone enters the carriage, the exemplary sensor unit of the present disclosure (200) may be configured to collect relevant data by detecting the brightness and the infrared ray of the human body, by, for example, selecting/activating the brightness sensor and the human pyroelectric infrared sensor.

For example, the at least some embodiments of the present disclosure may utilize the transport equipment data to determine, in real-time, a location specific, equipment-specific energy usage what may be further utilized to predict, in real-time, equipment breakdown and automatically generate, in real-time, the inventive remedial cargo quality instruction(s) that consider the predicted equipment breakdown. For example, the inventive remedial cargo quality instruction(s) may be configured to affect the location specific level of energy usage of the specific cargo equipment (e.g., at least one instruction to adjust at least one of at least one operational parameter). For example, the inventive remedial cargo quality instruction(s) may identify that a server of the cargo control center stops receiving sensor data and/or cargo transport equipment data.

In some embodiments and, optionally, in combination of any embodiment described above or below, exemplary sensors(s) of the present disclosure may sense and record any changes to physical integrity of the transported good(s) or goods in storage (e.g., sealed condition of a bottle with spirit) and/or its transporting packaging (e.g., a case/box packaging for transporting spirits, a pallet, a container, etc.). In some embodiments and, optionally, in combination of any embodiment described above or below, exemplary sensors(s) of the present disclosure may sense and record any changes affecting the expected operation of a transporting vehicle or goods in storage (e.g., ship, train, truck, warehouse, etc.). For example, at least some exemplary sensors of the at least some embodiments of the present disclosure may be configured to store visual and/or audio input (e.g., images of the items being shipped or stored). In some embodiments and, optionally, in combination of any embodiment described above or below, the exemplary inventive computer-based system of the present disclosure may be configured to utilize the visual/audio input to dynamically and electronically track, for example, physical integrity of the transported or stored items/goods (e.g., as the items are being packed, to track that the items are in good condition before, during, and/or after a shipment).

In some embodiments and, optionally, in combination of any embodiment described above or below, in addition to the environmental attribute(s), the exemplary sensors(s) of the at least some embodiments of the present disclosure may record time(s) at which particular environmental attribute(s) has/have been measured. In some embodiments and, optionally, in combination of any embodiment described above or below, in addition to the environmental attribute(s) and the corresponding time(s), the exemplary sensors(s) of the at least some embodiments of the present disclosure may record at least one of: a location of a sensor, location(s) at which particular environmental attribute(s) has/have been measured, and any combination thereof.

In some embodiments and, optionally, in combination of any embodiment described above or below, the at least some embodiments of the present disclosure may utilize active memory devices (e.g., electronic or magnetic memory as opposed to barcodes, which are a passive memory) that have additional features such as global positioning and/or environmental sensors (e.g., temperature, humidity, vibration/shock, sound, light, air contaminants, pH, location, odors, gases, and etc.) may also be implemented as part of the memory devices.

For example, the memory device for a particular container may include a microprocessor (or microcontroller) and a temperature sensor. The microprocessor may be configured to periodically sample the temperature readings from the sensor. If the temperature exceeds a predetermined threshold (e.g., too low or too high), then the processor may store an indication of this (e.g., the exact temperature and the time that the event took place) in the memory device. Alternatively, the processor may be configured to store all periodic temperature readings in the memory device, thereby providing the recipient and the shipping company with a complete log of the temperatures experienced by the container throughout the shipping process. Taking the wireless connection one step further, the memory device may be configured with a long-range wireless communications device (e.g., with a cellular or PCS telephone link, satellite link, or other wireless network protocol) to allow the memory device to periodically upload the temperature or other environmental information and the data file to central server or to log the data in the sensor memory for later retrieval. In embodiments where the memory device includes other environmental sensors, other environmental data may be recorded in the memory device and/or transmitted via a wireless link. In one embodiment, central server may be included in an intelligent shipping agent system. An intelligent shipping agent may be implemented in software configured to execute on a system of one or more computers coupled by a network. The software may be configured to arrange shipment and insurance for items being shipped or mailed.

Sensor device can be tamper proof to prevent resetting, unauthorized recalibration, or other modification by unauthorized parties as to affect the data.

In some embodiments and, optionally, in combination of any embodiment described above or below, exemplary sensors(s) of the at least some embodiments of the present disclosure may sense and/or record one or more operational parameters of equipment (e.g., based on IP address of such equipment) that is involved in the cargo transport and/or storage such as, without limitation, cargo transporter (e.g., truck, ship, plane) and/or cargo containers (e.g., refrigerated containers (reefers), etc.).

Figure 2B:
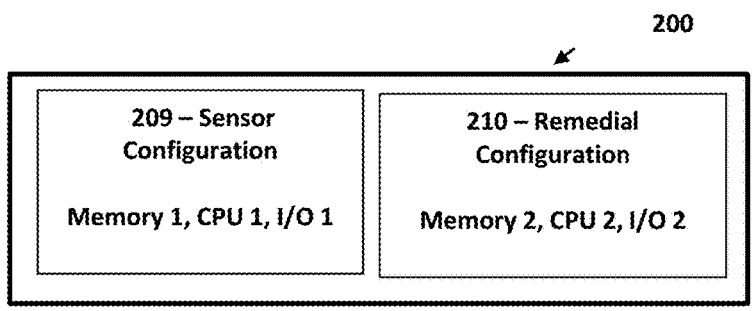

In some embodiments and, optionally, in combination of any embodiment described above or below, as shown in FIG. 2B, the exemplary sensors(s) of the at least some embodiments of the present disclosure may be configured to have a dual-purpose configuration. For example, the exemplary inventive sensors of the at least some embodiments of the present disclosure may have at least two functionally-separate types of hardware-software configurations (209 and 210) resided within a single housing (200). For example, one or more first type hardware-software configurations (209) may have dedicated memory, processing, and/or communication (Input/Output—I/O) capabilities to relay out the cargo transport-related sensor and/or operational data to, for example, a cargo transport command center. In turn, one or more second type hardware-software configurations (210) of the same inventive sensor may have dedicated memory, processing, and/or communication capabilities to receive, implement, and/or cause to implement one or more remedial instructions (i.e., the real-time automatic positive feedback loop) that would result in at least one actual (e.g., physical) change in at least one operational parameter of the equipment involved in the cargo transport to reduce and/or eliminate, in real-time, a negative impact on the quality of the cargo that being sensed and/or about to occur based on one or more predicted parameters as detailed herein.

In some embodiments, multiple sensors may be included in one shipment as to improve the accuracy in data measurement. In some embodiments, multiple sensors, of the same and/or different types, may be placed on the same packaging at different places. In some embodiments, multiple sensors, of the same and/or different types, may be placed within the same cargo container. In some embodiments, multiple sensors, of the same and/or different types, may be placed within the same cargo storage. In some embodiments, multiple sensors, of the same and/or different types, may be placed in a vicinity of the cargo. In some embodiments, the vicinity is from 1 millimeter to 25 meters away. In some embodiments, the vicinity is from 1 millimeter to 1 meter away. In some embodiments, the vicinity is from 1 centimeter to 1 meter away. In some embodiments, multiple sensors, of the same and/or different types, may be utilized to obtain historical data over the entire supply chain to allow the use of such supply chain historical data in determining a loss history (shortage shortfall history) for any of a particular storage, a particular shipper, a particular supplier (insured), a particular product, a particular mode of transport, a particular cargo container, a particular product packaging, and any combination thereof.

In some embodiments, the exemplary inventive systems of the present disclosure may electronically acquire/receive one or more expert opinions regarding the entire supply chain to allow the use of such supply chain expert opinion data with or without any other suitable data (e.g., the supply chain historical data) in determining a loss benchmark/standard (shortage shortfall benchmark) for any of a particular storage, a particular shipper, a particular supplier (insured), a particular product, a particular mode of transport, a particular cargo container, a particular product packaging, and any combination thereof.

In some embodiments and, optionally, in combination of any embodiment described above or below, the term "mobile electronic device" may refer to any portable electronic device that may or may not be enabled with location tracking functionality. For example, a mobile electronic device can include, but is not limited to, a mobile phone, Personal Digital Assistant (PDA), Blackberry™, Pager, Smartphone, or any other reasonable mobile electronic device. For ease, at times the above variations are not listed or are only partially listed; this is in no way meant to be a limitation.

In some embodiments and, optionally, in combination of any embodiment described above or below, the terms "proximity detection," "locating," "location data," "location information," and "location tracking" as used herein may refer to any form of location tracking technology or locating method that can be used to provide a location of, for example, a particular sensor or other component of the exemplary inventive system of the present disclosure, based, at least in part, on one or more of the following techniques, without limitation: Global Positioning Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

For example, a GPS-equipped sensor may be configured to store position data at any granular level (e.g., item/good level, unit of transportation level (e.g., case, pallet), contained level, transport level (e.g., ship, truck, etc.).

In some embodiments and, optionally, in combination of any embodiment described above or below, one or more sensors and/or sensor-associated devices utilized within the exemplary inventive computer-based system of the present disclosure may be configured to transmit the sensory data using any wireless communication modes, such as, without limitation: NFC, RFID, Narrow Band Internet of Things (NBIOT), 3G, 4G, 5G, GSM, GPRS, WiFi, WiMax, CDMA, satellite, ZigBee, and other suitable communication modes.

In some embodiments and, optionally, in combination of any embodiment described above or below, one or more sensors and/or sensor-associated devices utilized within the exemplary inventive computer-based system of the at present disclosure may be configured to employ near-field/frequency peer-to-peer communication (NFC) to, for example without limitation, to aggregate sensory data from a network of low-power sensors at a particular location within a transportation vehicle to an axillary transmitting device that may be programmed to transmit the sensory data over long distances by employing, for example without limitation, satellite-based data transmission.

In some embodiments and, optionally, in combination of any embodiment described above or below, one or more sensors and/or sensor-associated devices utilized within the exemplary inventive computer-based system of the present disclosure may be configured to include a cellular transceiver coupled to a processor and receiving a cellular network timing signal. In some embodiments and, optionally, in combination of any embodiment described above or below, one or more sensors and/or sensor-associated devices utilized within the exemplary inventive computer-based system of the present disclosure may be configured to include a satellite positioning receiver coupled to the processor and receiving a satellite positioning system timing signal, and the processor may accordingly be configured to synchronize the internal timing signal to the satellite positioning system timing signal as the external timing signal.

In some embodiments and, optionally, in combination of any embodiment described above or below, one or more sensors and/or sensor-associated devices utilized within the exemplary inventive computer-based system of the present disclosure may include a location module that is configured to determine, alone or in combination with a remote server, a current location of each sensor and/or the cargo transport vehicle. In some embodiments, the location module may receive cellular signals from the multiple cell towers and uses the received signals to calculate a location of the transport vehicle. For example, the location module may use cellular triangulation using the multiple cell towers providing the strongest signal to the exemplary sensor. For example, the location module may determine characteristics of the cell signals and use the characteristics to calculate the location. For example, the location module may calculate a received signal strength indication (RSSI) of the signals and use the RSSI to calculate the location of the transport vehicle (e.g., based on a determination that stronger signals indicate a closer proximity to a known location of a cell tower, and weaker signals indicate a farther proximity from the cell tower). In some embodiments, cellular signal characteristics other than RSSI may be used alone or in combination with RSSI.

In some embodiments, the location module may use other types of transceivers or sensors to help determine a location of each sensor, storage, and/or transport, alone or in combination with cellular signals. For example, a particular sensor device of the present disclosure may include a GPS transceiver configured to receive one or more GPS signals and determine a position of the particular sensor device using the signals. In some examples, a particular sensor device of the present disclosure may include a Wi-Fi transceiver, Bluetooth transceiver, RFID transceiver, and/or other long or short-range communication interface, and may determine its position using the data received via such communication interfaces. In one embodiment, a particular sensor device of the present disclosure may use cellular signals as a primary source for determining its position geographically and/or within a storage or transport, and may use location data received from other secondary sources to confirm and/or refine its location determined using the cellular signals.

In some embodiments and, optionally, in combination of any embodiment described above or below, one or more sensors and/or sensor-associated devices utilized within the exemplary inventive computer-based system of the present disclosure may be configured to include a power source, a circuit configured to wirelessly communicate using one or more suitable communication protocol. In some embodiments and, optionally, in combination of any embodiment described above or below, the processor of an exemplary NFC-enabled sensor and/or a sensor-associated device may be configured to synchronize an internal timing signal to an external timing signal, cycle power to the NFC circuit to periodically switch the NFC circuit between a peer-to-peer recognition state and a low power state based upon the synchronized internal timing signal, and initiate peer-to-peer NFC communications with another NFC-enable sensor and/or a NFC-enable sensor-associated device when in range thereof and upon being simultaneously switched to the peer-to-peer recognition state therewith.

In some embodiments and, optionally, in combination of any embodiment described above or below, one or more sensors and/or sensor-associated devices utilized within the exemplary inventive computer-based system of the present disclosure may be configured to include a related physical computer-readable medium and may have computer-executable instructions for causing a NFC-enable sensor and/or a NFC-enable sensor-associated device to initiating peer-to-peer NFC communications with another NFC device when in range thereof and upon being simultaneously switched to the peer-to-peer recognition state therewith.

In some embodiments and, optionally, in combination of any embodiment described above or below, one or more sensors and/or sensor-associated devices utilized within the exemplary inventive computer-based system of the present disclosure be configured to securely store and/or transmit sensory data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTRO, SHA-1, SHA-2, Tiger (TTH), WHIRLPOOL, RNGs).

In some embodiments and, optionally, in combination of any embodiment described above or below, the sensor data of the present disclosure may be store in one or more private and/or private-permissioned cryptographically-protected, distributed databased such as a blockchain (distributed ledger technology), Ethereum (Ethereum Foundation, Zug, Switzerland), and/or other similar distributed data management technologies. For example, as utilized herein, the distributed database(s), such as distributed ledgers ensure the integrity of data by generating a chain of data blocks linked together by cryptographic hashes of the data records in the data blocks. For example, a cryptographic hash of at least a portion of data records within a first block, and, in some cases, combined with a portion of data records in previous blocks is used to generate the block address for a new digital identity block succeeding the first block. As an update to the data records stored in the one or more data blocks, a new data block is generated containing respective updated data records and linked to a preceding block with an address based upon a cryptographic hash of at least a portion of the data records in the preceding block. In other words, the linked blocks form a blockchain that inherently includes a traceable sequence of addresses that can be used to track the updates to the data records contained therein. The linked blocks (or blockchain) may be distributed among multiple network nodes within a computer network such that each node may maintain a copy of the blockchain. Malicious network nodes attempting to compromise the integrity of the database must recreate and redistribute the blockchain faster than the honest network nodes, which, in most cases, is computationally infeasible. In other words, data integrity is guaranteed by the virtue of multiple network nodes in a network having a copy of the same blockchain. In some embodiments, as utilized herein, a central trust authority for sensor data management may not be needed to vouch for the integrity of the distributed database hosted by multiple nodes in the network.

In some embodiments and, optionally, in combination of any embodiment described above or below, one or more sensors and/or sensor-associated devices utilized within the exemplary inventive computer-based system of the present disclosure may be configured to perform a particular way based on a type of conditioned cargo space such as, without limitation, a transport (e.g., truck, ship, airplane, etc.), a cargo storage, a housing type enclosure used for cargo transport and/or cargo storage (e.g., dry container vs. "reefer"-type container), a short or long term storage facility (e.g., a warehouse, storage tank, or freezer), etc.

In some embodiments and, optionally, in combination of any embodiment described above or below, depending on a nature of the transported items/goods (e.g., perishable liquids (e.g., milk), nonperishable flammable liquids (e.g., fuel), agricultural commodities (e.g., sugar, wheat, etc.), etc.), the exemplary inventive computer-based system of the present disclosure may be configured to recommend at least one of:
i) type(s) of one or more sensors and/or sensor-associated devices to be used,
ii) placement location(s) of one or more sensors and/or sensor-associated devices with respect to the transported and/or stored items/goods,
iii) mode(s) of affixing one or more sensors and/or sensor-associated devices to the transported and/or stored items/goods.

For example, for transporting a large item (e.g., oil/gas drilling risers), exemplary sensor-associated devices may be vibration dampening devices.

In some embodiments and, optionally, in combination of any embodiment described above or below, the exemplary inventive computer-based system of the present disclosure may be configured to process the sensory data in accordance with one or more item/good-specific protocol and predetermined metrics, store the processed data, and transformed the processed sensory data into at least one of:
i) at least one alert (e.g., audible alert, visual alert, etc.) to a predetermined party (e.g., insured, shipper, etc.), and
ii) at least one visually presentation (e.g., a graph tracking, in real-time, a quality metric based on measured time over time, etc.).

In some embodiments and, optionally, in combination of any embodiment described above or below, the exemplary inventive computer-based system of the present disclosure may be configured to utilize one or more predictive algorithms to generate risk management recommendations based on processing sensory logistics and one or more of suitable factors detailed herein to prevent or mitigate loss. In some embodiments and, optionally, in combination of any embodiment described above or below, illustrative suitable factors may be, without limitation, historical piracy data, historical terrorist data, historical natural disaster data, historical political risk data, weather, news (e.g., strike announcements), etc.

In some embodiments and, optionally, in combination of any embodiment described above or below, the exemplary inventive computer-based system of the present disclosure may be configured to manage a digital on-line portal that may allow, for example without limitation, at least one of the following activities:
i) purchase a transportation or conditioned storage policy in real-time, and
ii) obtain stored data such as, without limitation, real-time sensory data, historical piracy data, historical terrorist data, historical natural disaster data, weather, news (e.g., strike announcements), and/or etc.

In some embodiments and, optionally, in combination of any embodiment described above or below, the exemplary inventive computer-based system of the present disclosure may be configured to determine a historical quality metric for a transported good/item from the historical transport data. In some embodiments and, optionally, in combination of any embodiment described above or below, the exemplary inventive computer-based system of the present disclosure may be configured to further transform the historical quality metrics into insurance metric parameters to dynamically determine an insurance premium associated with a particular shipment or series of shipments. In some embodiments and, optionally, in combination of any embodiment described above or below, the exemplary inventive computer-based system of the present disclosure may be configured to dynamically obtain and process the sensory data to determine current quality metric of the shipment during the transport and/or upon a completion of at least one transport leg. In some embodiments and, optionally, in combination of any embodiment described above or below, the exemplary inventive computer-based system of the present disclosure may be configured to dynamically obtain and process the sensory data to dynamically determine, for example without limitation, a validity of sensory data, a difference between the historical and current quality metrics (the quality shortfall), a validity of any claim concerning the quality shortfall, and, based on the verified quality shortfall, dynamically determine a remedial action (e.g., payout, resale, liquidation, etc.).

In some embodiments and, optionally, in combination of any embodiment described above or below, the at least some embodiments of the present disclosure may be utilized for tracking/monitoring a physical condition and/or environmental condition(s) that affect(s) the physical, biological, or chemical condition of numerous types of goods, including, without limitation, temperature controlled goods (TCG) which are goods such as, without limitation, fine art, pharmaceuticals, frozen foods, refrigerated foods, and etc. For example, cargo transport conditions (including cargo being transported and/or stored) can influence cargo commercial value of durable goods and/or pharmaceuticals. For example, in the knowledge of cargo shocks, temperature, and humidity can provide valuable insights for the owner to help reduce the uncertainty regarding cargo transport handling of fine art, certain construction materials, electronics, and textiles.

Figure 3:
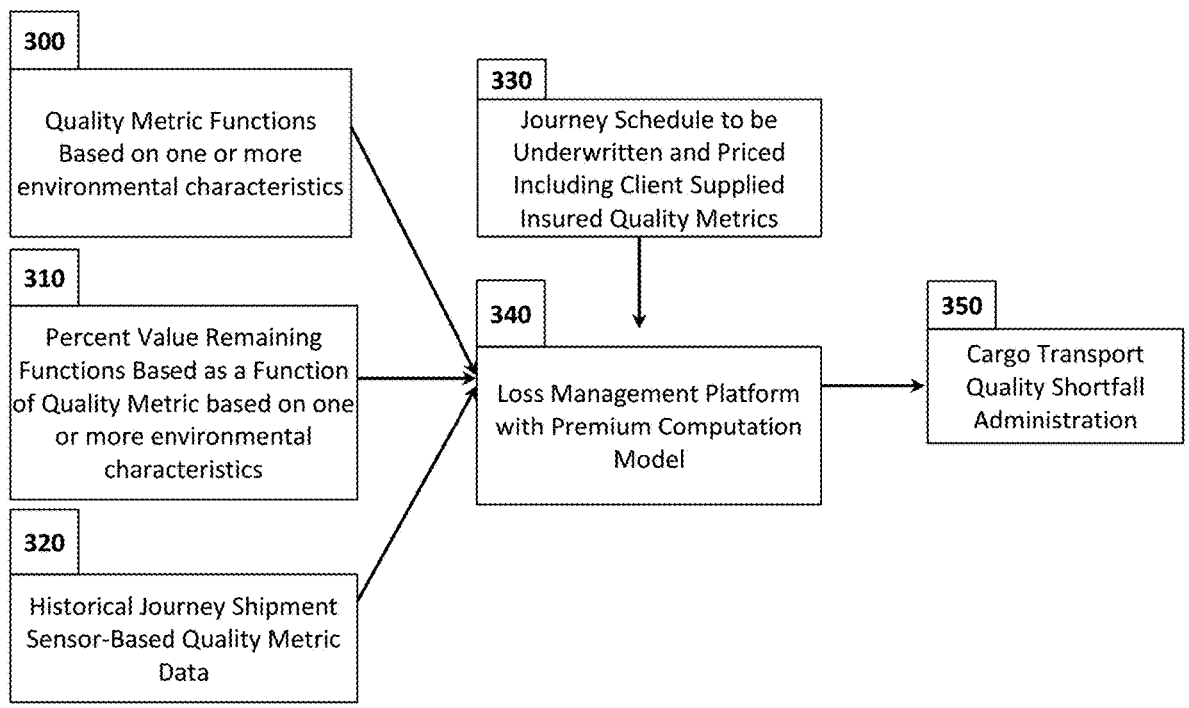
FIG. 3 is a flow diagram describing exemplary process steps associated with transforming sensor-collected environmental data into quality metrics to be utilized in accordance with at least some embodiments of the present disclosure.

FIG. 3 is flowchart showing an illustrative example of how the collected and compiled sensor data may be used to manage losses. In step 300, the environmental sensor parameters (e.g., temperature, humidity, shock, etc.) are determined/selected by, for example, based on how one or more environmental characteristics may influence the quality of the cargo being transported and/or stored. In some embodiments and, optionally, in combination of any embodiment described above or below, an exemplary inventive quality metric may be based at least in part on a relationship between the time-based sensor environmental data for a given cargo type and effective remaining quality of the cargo.

In step 310, the score values are related to percent remaining value. These functions are mainly based on the economics and type of the cargo being transported and/or stored. For example, for wines, excessive temperatures erode the quality of the wine but the degradation in quality is not realized until the wine is consumed at perhaps a much later time than when it was shipped. In this situation, the exemplary inventive computer-based system of the present disclosure may be configured to obtain and utilize a function of industry quality metric. For example, in some embodiments and, optionally, in combination of any embodiment described above or below, the exemplary inventive computer-based system of the present disclosure, executing the exemplary inventive cargo quality shortfall administration software, may be configured to utilize one or more wine quality metrics (e.g., wine chemical composition, etc.) based on time and temperature profiles provided, without limitation, by Jung et al., "Potential wine ageing during transportation," in BIO Web of Conferences 3, EDP Sciences (2014).

In some embodiments and, optionally, in combination of any embodiment described above or below, for perishable goods where the time to consumption is short, temperature fluctuations can cause premature ripening which reduces or perhaps eliminates market sales. In these situations, the quality metric to percent remaining value may be based at least in part on the time the cargo is expected to remain on the shelf for sale. And any reduction in that time would be reflected in a percent reduction in value.

In step 320 historical data for a given cargo type for a given quality metric function and a given percent remaining value equation is compiled. In some embodiments and, optionally, in combination of any embodiment described above or below, this data may quantify the historical quality shortfall performance for shipping a given cargo type that is to be rated and priced for a given shipper.

In some embodiments and, optionally, in combination of any embodiment described above or below, step 320 may be omitted in favor of receiving data related to estimated probabilities of achieving a given quality metric.

In step 330, the shipping schedule is compiled. In some embodiments and, optionally, in combination of any embodiment described above or below, the shipping schedule may contain the shipper's name and shipment data on each shipment for which the inventive cargo transport quality shortfall administration is desired. In some embodiments and, optionally, in combination of any embodiment described above or below, the shipment data for the inventive cargo transport quality shortfall administration may include: the source and destination, insured financial value, insured quality metric, type of coverage, and the salvage value if required.

In step 340, the exemplary quality function, the exemplary percent remaining value function, the exemplary historical quality data and exemplary coverage type are processed by the loss management and pricing platform that may enable a user to add risk modification attributes that are unique to the shipper into the premium calculations. In some embodiments and, optionally, in combination of any embodiment described above or below, the loss management model may be based at least in part on is Monte Carlo method of computational algorithms (e.g., the Solovay-Strassen type algorithms, the Baillie-PSW type algorithms, the Miller-Rabin type algorithms, and/or Schreier-Sims type algorithms) that may consider the historical quality data for the desired source-destination journeys and/or the user's experience for such journeys, the insured quality metrics, coverage type and/or the user entered risk modification factor(s). In some embodiments and, optionally, in combination of any embodiment described above or below, the exemplary quality function of the exemplary loss management model may be continuously trained by, for example without limitation, applying at least one machine learning technique (such as, but not limited to, decision trees, boosting, support-vector machines, neural networks, nearest neighbor algorithms, Naive Bayes, bagging, random forests, etc.) to the collected and/or compiled sensor data (e.g., various type of visual data about environmental and/or cargo's physical/visual appearance). In some embodiments and, optionally, in combination of any embodiment described above or below, an exemplary neutral network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of Neural Network may be executed as follows:

i) Define Neural Network architecture/model,
ii) Transfer the sensor data to the exemplary neural network model,
iii) Train the exemplary model incrementally,
iv) determine the accuracy for a specific number of timesteps,
v) apply the exemplary trained model to process the newly-received sensor data,
vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

In some embodiments and, optionally, in combination of any embodiment described above or below, an exemplary connection data for each connection in the exemplary neural network may include at least one of a node pair or a connection weight. For example, if the exemplary neural network includes a connection from node N1 to node N2, then the exemplary connection data for that connection may include the node pair <N1, N2>. In some embodiments and, optionally, in combination of any embodiment described above or below, the connection weight may be a numerical quantity that influences if and/or how the output of N1 is modified before being input at N2. In the example of a recurrent network, a node may have a connection to itself (e.g., the connection data may include the node pair <N1, N1>).

In some embodiments and, optionally, in combination of any embodiment described above or below, the exemplary trained neural network model may also include a species identifier (ID) and fitness data. For example, each species ID may indicate which of a plurality of species (e.g., cargo's loss categories) the model is classified in. For example, the fitness data may indicate how well the exemplary trained neural network model models the input sensory data set. For example, the fitness data may include a fitness value that is determined based on evaluating the fitness function with respect to the model. For example, the exemplary fitness function may be an objective function that is based on a frequency and/or magnitude of errors produced by testing the exemplary trained neural network model on the input sensory data set. As a simple example, assume the input sensory data set includes ten rows, that the input sensory data set includes two columns denoted A and B, and that the exemplary trained neural network model outputs a predicted value of B given an input value of A. In this example, testing the exemplary trained neural network model may include inputting each of the ten values of A from the input sensor data set, comparing the predicted values of B to the corresponding actual values of B from the input sensor data set, and determining if and/or by how much the two predicted and actual values of B differ. To illustrate, if a particular neural network correctly predicted the value of B for nine of the ten rows, then the exemplary fitness function may assign the corresponding model a fitness value of 9/10=0.9. It is to be understood that the previous example is for illustration only and is not to be considered limiting. In some embodiments, the exemplary fitness function may be based on factors unrelated to error frequency or error rate, such as number of input nodes, node layers, hidden layers, connections, computational complexity, etc.

Typically, resource-constrained environments (e.g., low-power or no-power sensors) have also been considered inappropriate environments for application of neural networks due to the intermittent communications often associated with such environments. Because a computing device in a resource-constrained environment may operate on low power, it may not be feasible to have an always-available communications link between the resource-constrained computing device (e.g., processor of low-power or no-power sensor) and other computing devices (e.g., the central data storage medium 120). Further, because a computing device in a resource-constrained environment may be a low cost embedded device, it may not be desirable to incur the financial cost and technical overhead of establishing an always-available communications link between the computing device and other computing devices. Further, because a computing device in a resource-constrained environment may move around widely, it may enter areas with reduced telecommunications infrastructure (e.g., lack of Wi-Fi and/or cellular networks) or areas with no authorized telecommunications infrastructure (e.g., outside the range of recognized Wi-Fi networks). This intermittent communications availability common in many resource-constrained environments has been considered an impediment to deploying neural networks, at least because it obstructed the ability to receive training data from the environment and then provide a trained neural network structure to the environment.

In some embodiments and, optionally, in combination of any embodiment described above or below, the exemplary neural network model receives input sensor values at input layer. In some embodiments and, optionally, in combination of any embodiment described above or below, the exemplary trained neural network model then propagates those values through connections to a particular layer. In some embodiments and, optionally, in combination of any embodiment described above or below, each of the connections may include a numerical weighting value (e.g., a value between −1 and 1) that is used to modify the original value (e.g., propagated value=original value*weight). In some embodiments and, optionally, in combination of any embodiment described above or below, nodes of the particular layer receive these propagated values as input. In some embodiments and, optionally, in combination of any embodiment described above or below, each node of the particular layer may include a function that combine the received input values (e.g., summing all received inputs). For example, each node may further contain one or more activation functions that determines when a value would be output on a connection of connections to the subsequent layer (e.g., output +1 if the combined value of the inputs is >0 and output −1 if the combined value of the inputs is <0, and output 0 if the combined value of the inputs is =0). Each node of an exemplary output layer may correspond to a predefined category for the input sensor values. For example, the combined input sensor values for each node of the output layer may determine a category determined for the input (e.g., the category for the output node that has the largest combined input values). In some embodiments and, optionally, in combination of any embodiment described above or below, in this way, the exemplary neural network structure may be used to determine a category for some sensor input.

In some embodiments and, optionally, in combination of any embodiment described above or below, weights for connections may be provided with default and/or random values to start. In some embodiments and, optionally, in combination of any embodiment described above or below, the sensor inputs are then provided to the exemplary neural network model through the input layer, and the determined categories for the sensor inputs (e.g., based on highest combined input values at the nodes of output layer) may be observed and compared to the correct categories as previously labeled. In some embodiments and, optionally, in combination of any embodiment described above or below, the weights for connections may be repeatedly modified until the exemplary neural network model correctly determines the correct categories for all inputs, or at least for an acceptable portion of all inputs, to result in the exemplary trained neural network model.

For example, when a new sensor input is received without a correct category previously determined, the exemplary inventive computer-based system of the present disclosure may be configured to submit that input to the exemplary trained neural network model to determine the most likely category for that input.

In some embodiments and, optionally, in combination of any embodiment described above or below, a label applied to input sensor data may be applied to a tuple of input data: <image, sensor data 1, sensor data 2, sensor data 3>. For example, a label provided for the input sensor data may not be specific to just an image provided as input. Rather, the label may be provided as applicable to the entire situation in the cargo as described by the image, the sensor data 1, the sensor data 2, and the sensor data 3. In some embodiments and, optionally, in combination of any embodiment described above or below, the image, sensor data 1, and sensor data 2, and sensor data 3 may all be captured in different parts of the cargo at approximately the same time. As an example, while an image input for a time t1 may show the condition of cargo at particular temperature and humidity level to be unspoiled at time t1, then the tuple for time t1 may be labeled "no loss," reflecting the fact that the cargo is in acceptable condition.

In some embodiments and, optionally, in combination of any embodiment described above or below, the exemplary neural network model may be trained in the non-resource-constrained environment using the transferred sensor data. In some embodiments and, optionally, in combination of any embodiment described above or below, the sensor data transferred from the resource-constrained environment may be labelled prior to or as part of the input data. In some embodiments and, optionally, in combination of any embodiment described above or below, the exemplary neural network model may be further optimized by, for example but not limited to, reducing a number of nodes, reducing a number of connections, reducing a file size of a file storing parameters defining the neural network model, or any combination thereof.

In step 350, the exemplary inventive computer-based system of the present disclosure may be configured to output a premium and execute the cargo transport quality shortfall administration for a particular shipment.

For an example of how to develop a quality metric function as depicted in FIG. 3 step 310, consider the cargo transport of the perishable good: bananas. In some embodiments and, optionally, in combination of any embodiment described above or below, the quality metric function may be based on bio-chemical reactions involved with the ripening of bananas as a function of temperature, humidity, and various other suitable environmental characteristics. The example here involves bananas grown in the tropics in Central America, packaged, and transported by cargo ship to Europe via a two-week journey. For example, Kader, A. A. (2012): Banana: Recommendations for Maintaining Postharvest Quality, Produce fact sheets, UC Davis, Postharvest Technology (Kader) and Kerbel, E. (2004): Banana and Plaintain, Agriculture Handbook Number 66, The Commercial Storage of Fruits, Vegetables, and Florist and Nursery Stocks (Kerbel) have determined that the optimal storage for green bananas is 13-14° C. Storage at temperatures lower than this range produces chilling injury and exposure to temperatures greater than this range produces accelerated ripening. Broughton, W. J., Wu, K. F. (1979): Storage conditions and ripening of two cultivars of banana, Scientia Horticulturae, 10, 83-93 (Broughton and Wu) have shown that the optimal relative humidity ranges are in the range of 90 to 95%. Exposure to a lower relative humidity environment also reduces bananas' green-life period. And this example demonstrates the scientific to economic value process required to determine an exemplary quality metric that the exemplary inventive computer-based system of the present disclosure can utilize to execute the inventive cargo transport quality shortfall administration for temperature variations from the optimal range (13-14° C.). A similar process may be followed for humidity.

For example, Praeger, Ulrike et. al., "Effect of Storage Climate on Green-Life Duration of Bananas," 5th International Workshop—Cold Chain Management, June 2013, Bonn, Germany, have shown that the green-life period or optimal storage condition for bananas in an acceptable relative humidity environment, 98%, varies exponentially with storage temperature by the following equation (1):

$$\text{Average GreenLife Period} = 159.86 e^{-0.125 * T} \tag{1},$$

where T=storage temperature ° C.

Figure 11:
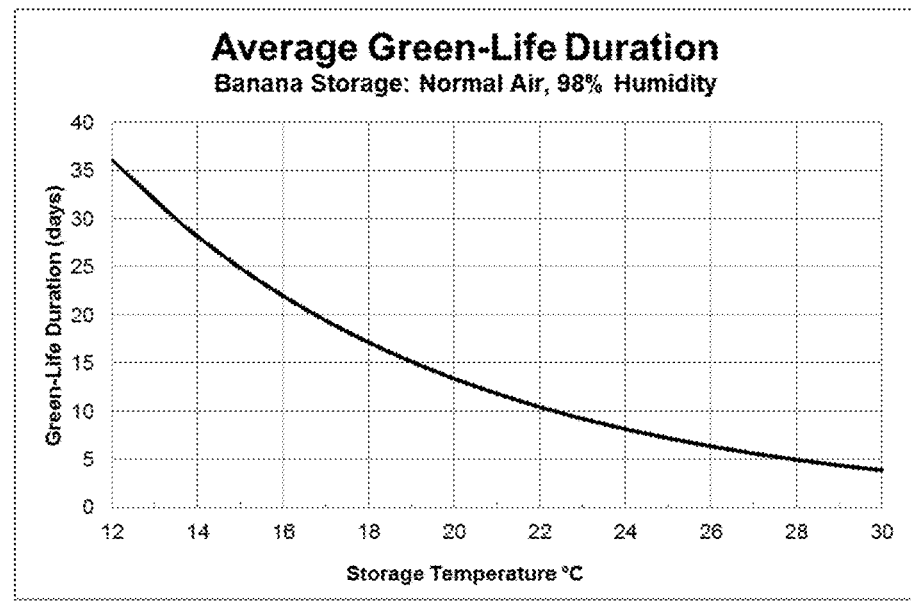

FIG. 11 shows an exemplary graph of this equation (1) for a practical, experienced-base temperature range for the two-week ocean transport journey.

The graph of FIG. 11 represents the scientific based data for developing a metric to represent the shipment quality associated with a given cargo. In some embodiments and, optionally, in combination of any embodiment described above or below, one or more variables (e.g. temperature, humidity, O2/CO2 and similarly suitable others) may be analyzed together to develop this green-life duration curve.

In some embodiments and, optionally, in combination of any embodiment described above or below, the exemplary inventive quality metric may be developed to represent the overall quality of the transported cargo. In some embodiments and, optionally, in combination of any embodiment described above or below, the exemplary inventive quality metric may be designed to indicate the effective remaining quality of the shipped cargo compared to a perfect or optimal journey environment.

In this example, since the optimal storage temperature is between 13-14° C., the exemplary inventive quality metric is taken as a ratio of equation (2):

$$\text{Banana Transport Score}(T) = 100 * \max\left\{1, \frac{159.86 e^{-0.125 * 14}}{159.86 e^{-0.125 * T}}\right\}. \tag{2}$$

For example, the equation (2) may be simplified to equation (3):

$$\text{Banana Transport Score}(T) = 100 * \max\{1, e^{-(0.125 * (T-14))}\} \tag{3}.$$

Figure 12:
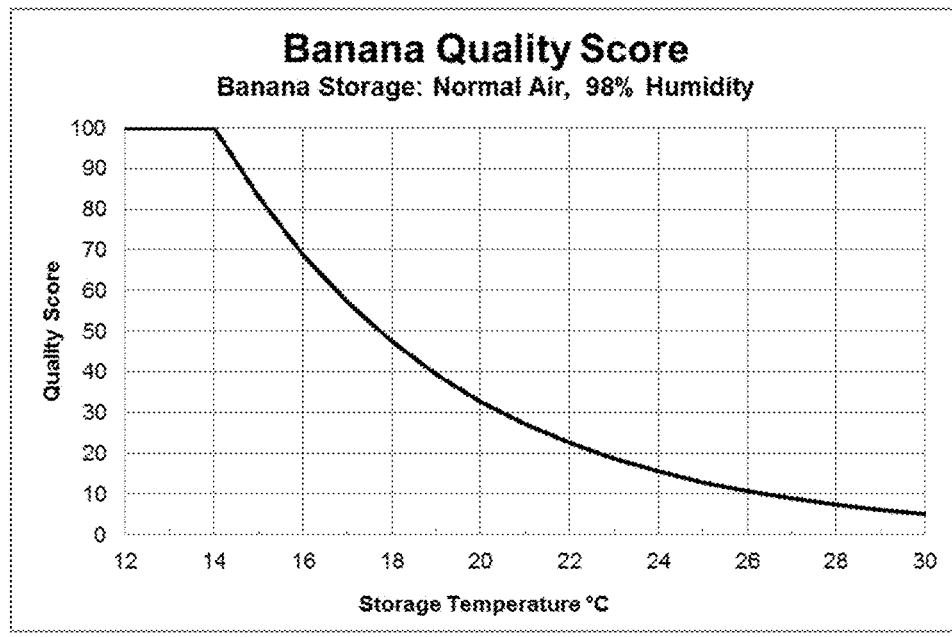

For example, the exemplary inventive quality metric as a function of the environmental temperature is shown in a graph of FIG. 12.

As an example of FIG. 3 step 320, In some embodiments and, optionally, in combination of any embodiment described above or below, the exemplary percent remaining value curve as a function of quality metric may be developed based at least in part on particular attribute(s) of the shipping process and/or cargo-related inputs received from the cargo's buyer.

Figure 13:
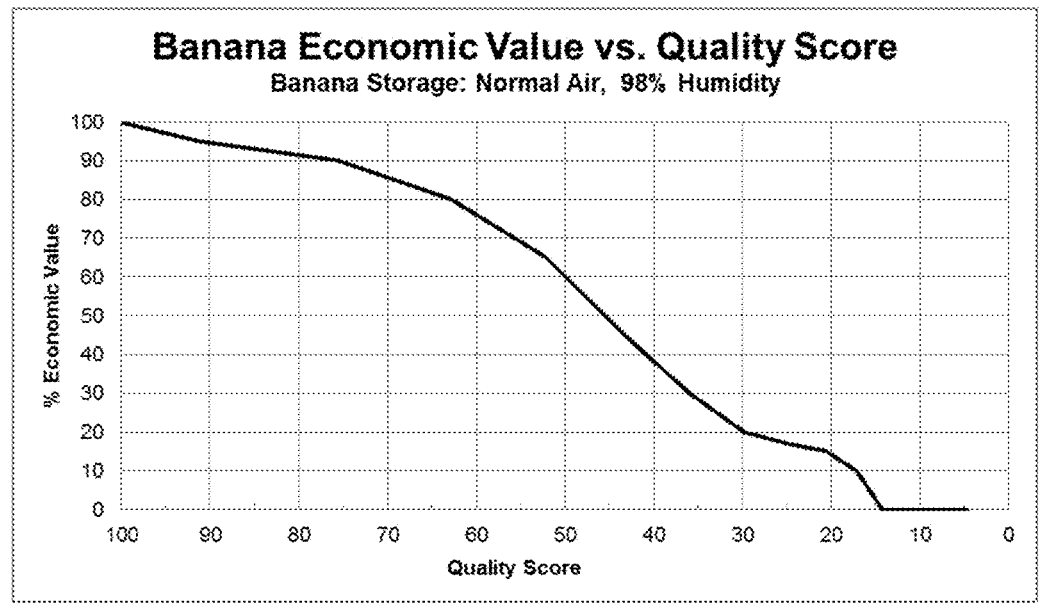

In this example, the marine transport process requires two weeks and the bananas are then distributed to various buyers by truck. FIG. 13 shows an exemplary graph of an exemplary curve that represents the remaining economic value as a function of the banana transport quality metric. An example of this function is shown in Graph 3.

The exemplary of FIG. 13 indicates a growing rate of declining value. For example, after the exemplary quality metric drops to 30 or below, shipments may be repurposed to alternative products rather than sold directly in supermarkets at considerably less value.

Figure 14:
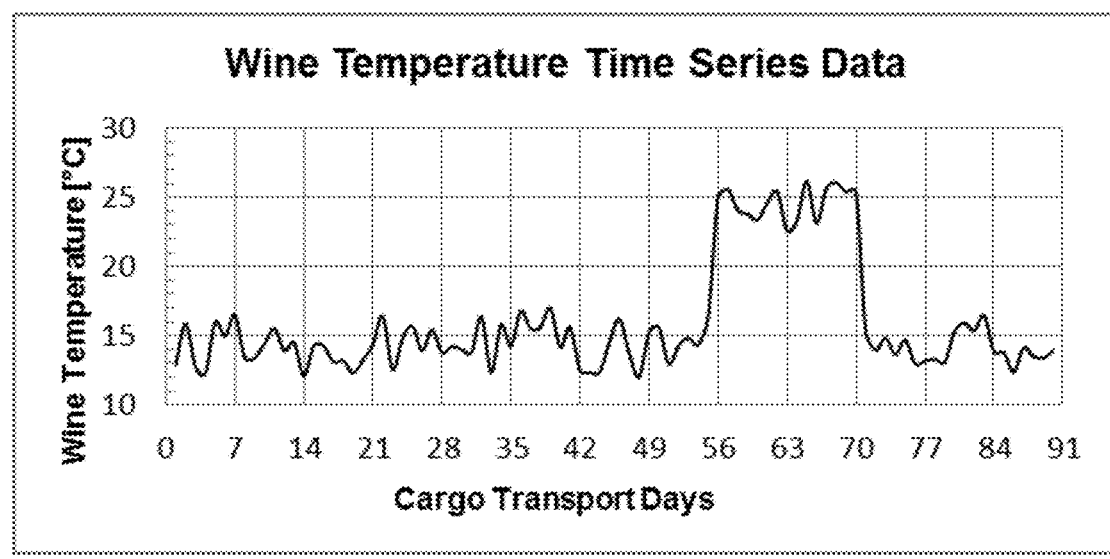

Another example of developing a quality metric from sensor obtained environmental data is presented for wine. In some embodiments and, optionally, in combination of any embodiment described above or below, that an exemplary quality metric for wine can be determined based at least in part on temperatures during the shipping and/or storage. For example, the exemplary quality metric for wine may be determined considering that the optimal storage temperature to be 12-15° C., depending on a wine type. For example, an exemplary wine cargo is being transported from France to stores in South America and the total journey time is 91 days or 13 weeks. FIG. 14 shows a graph representative of temperature data recorded and transmitted by sensor(s) during the exemplary journey.

In some embodiments and, optionally, in combination of any embodiment described above or below, the exemplary inventive computer-based system of the present disclosure may be configured to capture the time-series temperature exposure based on the concept of degree days. In some embodiments and, optionally, in combination of any embodiment described above or below, other suitable methods could also be applied to capture the temperature exposure of the shipped product, in this case, wine, from the sensor collected environmental data. For example, the temperature degree days (from 15° C.) exposure for the exemplary wine may be computed by the following formula (45):

$$\text{Temperature Degree Days} = \sum_{i=1}^{91} \max(T_i - 15, 0). \quad (4)$$

Figure 15:
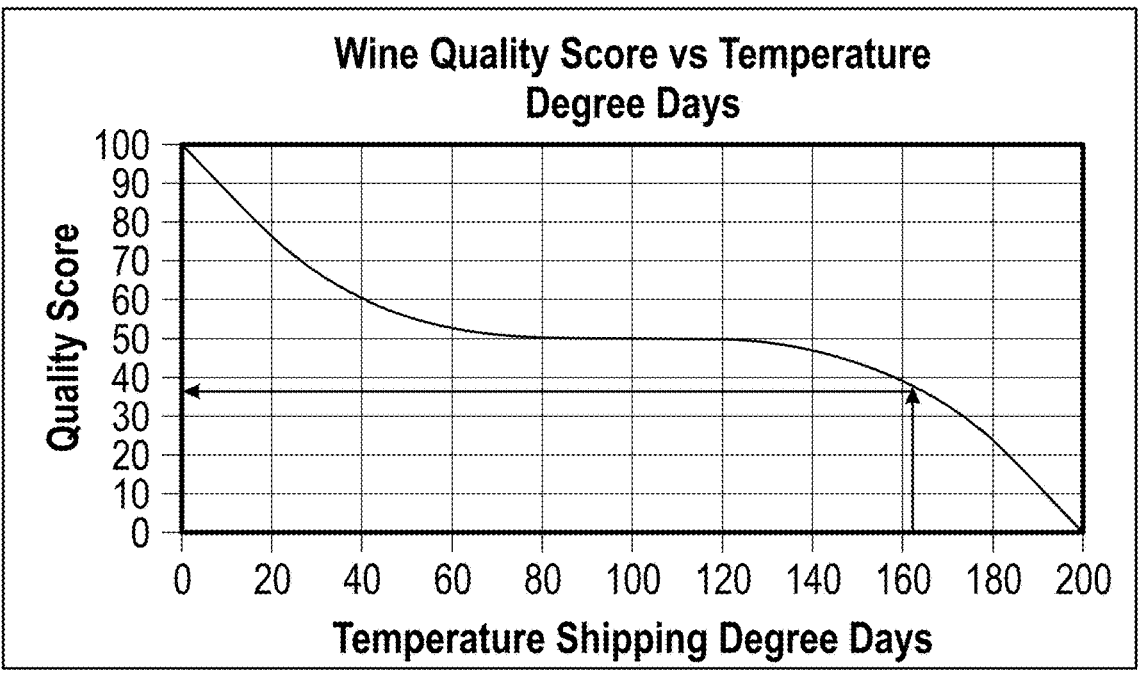

For example, the illustrative calculation yields a temperature degree day value of 162. This relatively high value was clearly caused by the temperature excursion which occurred for 2 weeks starting at day 56. In some embodiments and, optionally, in combination of any embodiment described above or below, the exemplary inventive computer-based system of the present disclosure may be configured to utilize a metric that quantifies the effect of this temperature excursion on wine quality. In some embodiments and, optionally, in combination of any embodiment described above or below, the exemplary wine quality curves detailed herein have been developed tracking transport conditions related to one or more wines identified in Table 1.

of the exemplary graph of FIG. 15 to determine the corresponding quality metric of 38.

From FIG. 3, at step 320, the exemplary inventive computer-based system of the present disclosure may be configured next step is to compute an example of the percent remaining value associated with this journey where the shipment started with a starting quality metric of 100, valued at the current market price, and has arrived at its destination with an ending quality metric of 38. In some embodiments and, optionally, in combination of any embodiment described above or below, the exemplary inventive computer-based system of the present disclosure may be configured to utilize the relationship between quality metric and percent remaining value for a wine and/or wine type that may be determined based at least in part on one of taste tastings, price elasticity, seller inventory turnover rates, and other suitable factors related to the sales of the shipped product. For this example, the exemplary inventive computer-based system of the present disclosure may be configured to utilize an exemplary curve shown in a graph of FIG. 16.

Figure 16:
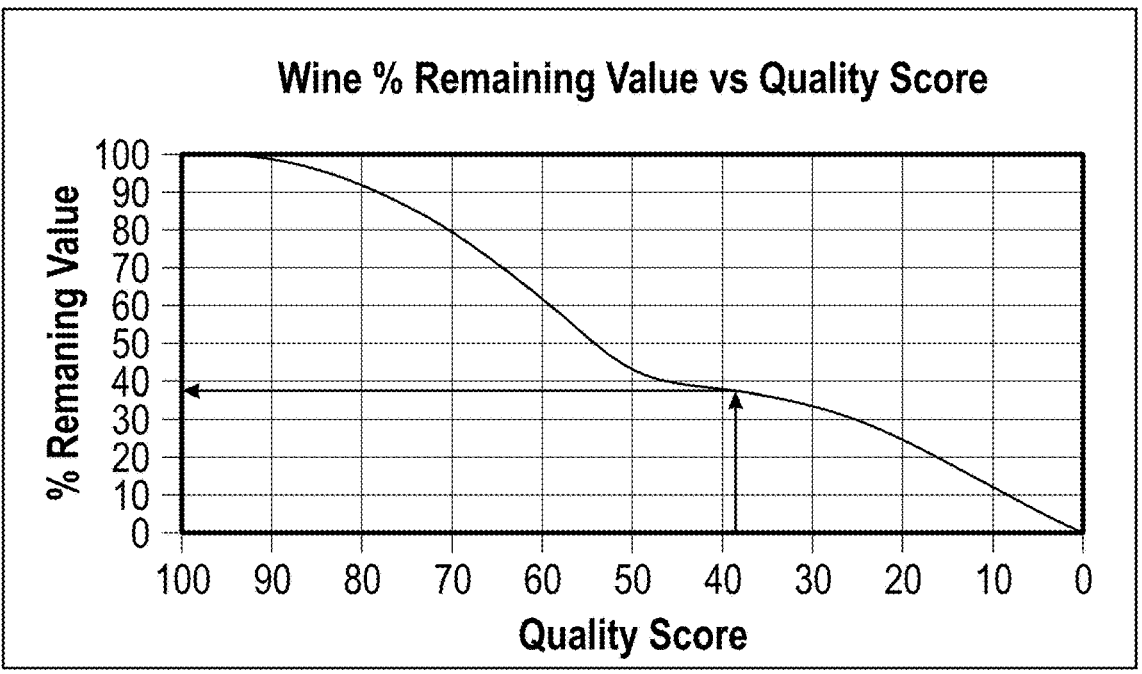

From the illustrative graph of FIG. 16, the exemplary quality metric of 38 corresponds to about 38% remaining value.

In some embodiments and, optionally, in combination of any embodiment described above or below, the exemplary inventive computer-based system of the present disclosure may be configured to utilize the exemplary inventive sensors to obtain data related to at least one specific wine attribute and/or at least one wine characteristic category. For example, the exemplary inventive sensor(s) of the present disclosure may be configured to track, in real-time, chemical composition of wine in one or more bottles by utilizing (1) one or more direct sensing methods via at least one sensor incorporated in a bottle; and/or (2) one or more indirect sensing methods via non-contact analyzers (e.g., Infrared chemical spectroscopy analyzer). In some embodiments and, optionally, in combination of any embodiment described above or below, the inventive tracking of the wine quality during the cargo transport and the generation of corresponding real-time remedial actions are based on individual quality attribute(s) rather than on the wine as a whole. For example, the invention may rely on wine's quality characteristic categories: Color, Smell, and Taste. In some embodiments and, optionally, in combination of any embodiment described above or below, the exemplary inventive computer-based system of the present disclosure may be configured to utilize the wine quality scoring that is

TABLE 1

| | Wine | Brand/Producer | Country/Region | Colour | Content |
|---|---|---|---|---|---|
| 1 | Reserve Exclusive brut 0.75 l | Champagne Nicolas Feuillatte | France/Champagne | W | 0.75 L |
| 2 | Das ist 100% Saale-Unstrut Sauvignon Blanc | Winzervereinigung Freyburg | Germany/Saale Unstrut | W | 0.75 L |
| 3 | Dark Horse Chardonnay | Ernest & Julio Gallo/Dark Horse | USA/California | W | 0.75 L |
| 4 | Capitor Bordeaux Spéciale | Castel/Capitor | France/Pays Bordeaux | R | 0.75 L |
| 5 | Pinot Noir (Spätburgunder) red wine, Year 2016 | Winery of the University of Geisenheim | Germany/Geisenheim | R | 0.75 L |

For example, in cases when the wine quality erodes as a function of temperature degree days as measured from the nominal, an exemplary ideal storage temperature may be 15° C. as depicted in a graph of FIG. 15.

To compute a quality metric for this journey, the exemplary inventive computer-based system of the present disclosure may be configured to use 162 on the horizontal axis based on numerical scores for each class from tasting studies. FIG. 22 shows a representative scoring system and exemplary percent remaining value assignments.

In some embodiments and, optionally, in combination of any embodiment described above or below, the exemplary inventive computer-based system of the present disclosure may be configured to utilize the exemplary wine category quality criteria that may have been agreed between parties to the cargo transport (e.g., shipper, insurer, insured) before shipments and can be utilized to generate real time remedial action(s) for the positive feedback.

In some embodiments and, optionally, in combination of any embodiment described above or below, the exemplary inventive computer-based system of the present disclosure may be configured to utilize the sensor collected journey temperature and other suitable sensor data to map the tasting results of known temperature(s) and other suitable sensor time series to specific scores. For example, similarly to the exemplary curve of FIG. 15 and, in at least in some embodiments, in addition to determination of the wine quality during the transit based on FIG. 15, specific time series may be applied to test wines and with the quality results obtained from tastings to obtain specific score and percent remaining value curves based on wine attribute(s) instead of the overall score.

In some embodiments and, optionally, in combination of any embodiment described above or below, the exemplary inventive computer-based system of the present disclosure may be configured to utilize the sensor collected temperature and/or other environmental conditions data to confirm the findings of the tastings. For example, when the insurance (e.g., a remedial action) is applied only to quality degradation during transport due to specific environmental condition(s), the sensor data may be used to verify that the tastings observed quality degradations are caused by insured perils and not due to other, uninsured causes.

In some embodiments and, optionally, in combination of any embodiment described above or below, the exemplary inventive computer-based system of the present disclosure may be configured to provide an active, real-time positive feedback in the cargo transport of the perishable foods based on the environmental transport quality. For example, FIG. 21 shows exemplary risk factors and their effects for the bulk transportation of potatoes. In some embodiments and, optionally, in combination of any embodiment described above or below, the exemplary inventive computer-based system of the present disclosure may be configured in accordance with rules defined FIG. 21. For example, items 2100, 2110, 2120, 2130, 2140, and 2150 denote the transport quality risk factors. Next to the risk factor labels, three categories are listed: Green, Yellow, and Red along with the corresponding environmental conditions definitions. As the environmental sensor data is received in real-time, the exemplary inventive computer-based system of the present disclosure may be configured to automatically calculate the score value based on FIG. 21 which may be representative of one of three situations: Green—no quality degradation, Yellow—partial quality degradation, or Red—major quality degradation. In step 2160, typical administrative data may be collected and in step 2170, the exemplary inventive computer-based system of the present disclosure may be configured to automatically generate, in real-time, a remedial action in a form of the corresponding compensation, if any. In some embodiments, parties to the perishable food cargo transport may agree that one or more Yellow conditions (e.g., a certain degree of degradation) would result in a compensation of X % of insured value minus deductible and/or one or more Red conditions would represent a claim of Y % of insured value minus deductible.

Another example of exemplary quality metrics and percent remaining value functions may be utilized for the transport of pharmaceuticals. For example, a particular drug Oxytocin is shipped around the world and used to prevent and treat post-partum hemorrhage. Research typically has shown that over a 96-day storage period, the time that it may take for Oxytocin to degrade to 90% of its initial potency ("The Effect of Temperature Changes on the Quality of Pharmaceutical Products During International Transportation," H. Farrugia, R. Brincat, MC. Zammit, F. Wirth, A. Serracino Inglott, University of Malta, Dept. of Pharmacy, Msida, Malta) may vary according the results in Table 2.

TABLE 2

| Storage Temperature ° C. | Time to Degrade (days) |
|---|---|
| 4 | 159 |
| 25 | 159 |
| 30 | 64 |
| 40 | 35 |
| 50 | 16 |

Figure 17:
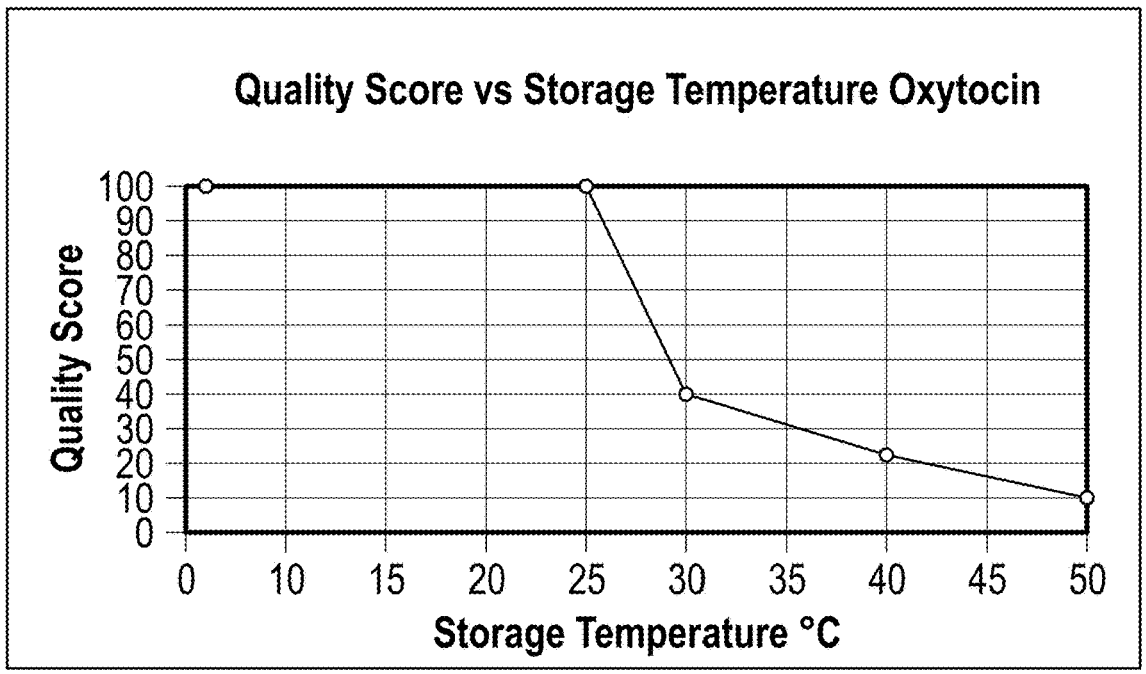

For this example, an exemplary quality metric can be defined as the ratio of the time to degrade and the initial time of 159 days. The quality metric as a function as storage temperature for this example is shown in an exemplary graph of FIG. 17.

In this example, the value of the drug is equal to its potency and the percent value remaining could be taken directly as the quality metric thereby eliminating the economic analysis required to develop the percent value remaining as a function of the quality metric. In this case, the potency lifetime is the remaining value and there is no additional economic analysis required. Still referencing FIG. 3, at step 320, the exemplary inventive computer-based system of the present disclosure may be configured to take the exemplary quality metric related to the transport of Oxytocin as the percent value remaining. The resultant score to value remaining function may be defined by the equation (5):

$$\text{percent value remaining} = \text{quality metric} \tag{5}$$

Figure 18:
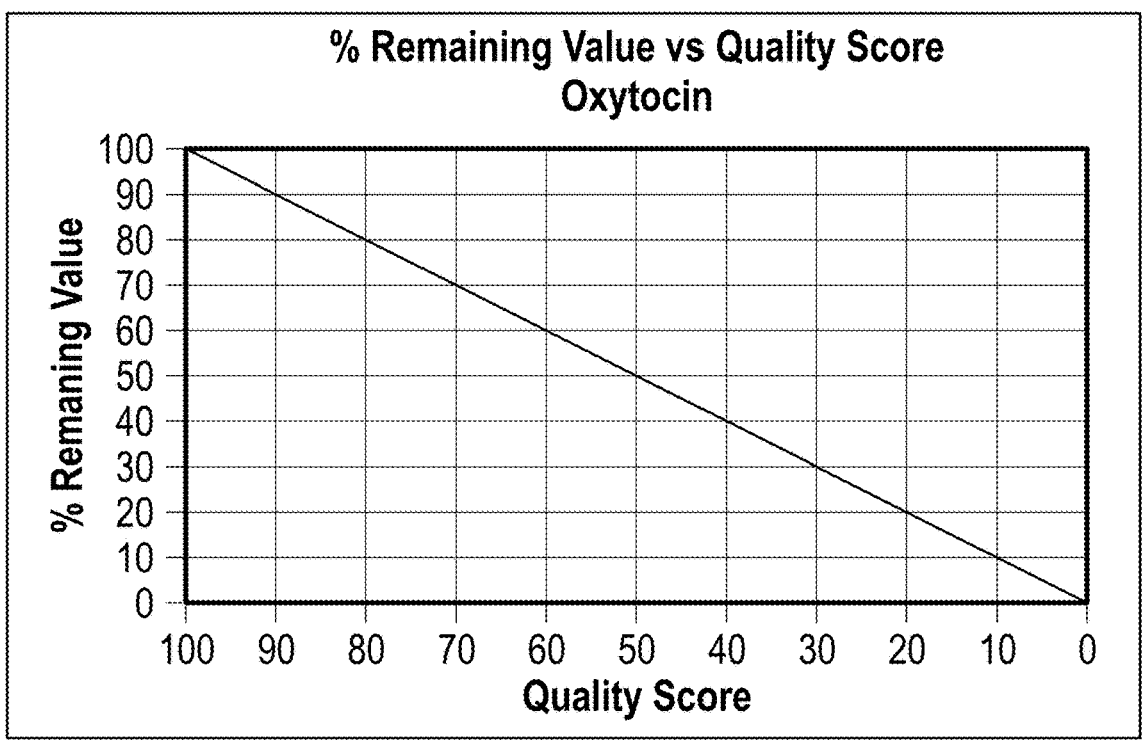

FIG. 18 shows an exemplary graph that is representative of the curve of the exemplary equation (5).

Another example for how sensor collected environmental data can be applied to create quality metric and percent economic value remaining, FIG. 3 steps 310 and 320, may be utilized for the inventive cargo transport quality shortfall administration for the shipment of fine art. For example, depending on the type of art being shipped temperature, humidity, shock, light, vibration, and other suitable environmental data may be collected via an array of sensors included in the packaged art.

In this example, we consider the transport of oil-based paintings where the main risk exposures are shock and vibrations. Shock effects, measured in terms of g forces, are a necessary exposure associated with movement of all cargo. For example, the transported paintings can experience 0.3-1.3G shocks during the road transport. For example, shocks in the range of 2-3G can be observed each time the shipping case is picked up or put down, for instance at customs or security checks, and illustrative shocks of 1.0-1.5G when the case is secured in the aircraft's cabin. However, it may be possible for a case to experience shocks in excess of 10G from mishandling during shipment. For example, the vibrational data can be monitored at multiple frequencies. For example, one or more accelerometers may monitor all frequencies within a given range (e.g. the range of the accelerometer), or a particular accelerometer may monitor a subset of frequencies. For example, the particular accelerometer may only monitor those frequencies associated with the most damage to a particular perishable good. For example, the amplitude of vibrations detected at each frequency can be monitored. In one embodiment, a particular accelerometer may detect vibrations in an X-direction, a Y-direction, and a Z-direction. Further, the exemplary accelerometer may monitor both peak amplitude of measured vibrations (Gpeak), as well as an RMS value (GRMS).

In some embodiments and, optionally, in combination of any embodiment described above or below, the exemplary inventive computer-based system of the present disclosure may be configured to utilize an exemplary functional relationship between shocks and fine art damage that may be dependent on one or more physical characteristics of the specific cargo being shipped. For example, one may assume, an illustrative example, that damage may be proportional to the frequency and severity of discrete shocks based at least in part on equation (6):

$$\text{Damage} \propto \int_0^T \alpha S(t) + \beta S^2(t) dt \quad (6),$$

where T is the total journey time, S(t) is the shock magnitude at time 't' of the journey, and α, β are suitable constants which may be pre-determined.

In some embodiments and, optionally, in combination of any embodiment described above or below, in addition to shocks, vibrations of the paintings during transport can cause cracking or weakening of the paint that may crack at a later time thereby reducing the quality and value of the art at a later time. For example, cracks may occur according to an exemplary exponential equation (7):

$$\text{\# of cracks formation} = \int_0^T e^{a+bx(t)+cx(t)^2} dt \quad (7),$$

where T is the total journey time; a, b, and c are suitable constants which may be pre-determined, and x is observed vibration acceleration (m/s2) as a function of time 't'.

In this example there are two environmental conditions that may be used together to compute an exemplary quality metric for fine art since either variable can cause damage. For example, one method of computing the quality metric for vibration and shock effects may be based at least in part on an equation (8):

$$\text{Quality metric} = A\int_0^T \alpha S(t) + \beta S^2(t) dt + B\int_0^T e^{a+bx(t)+cx(t)^2} dt \quad (8),$$

where A and B may be normalization constants to produce scores between 0 and 100.

For example, the exemplary fine art quality metric that is based on shock and vibration sensory data may be used to determine the percent remaining value. In some embodiments and, optionally, in combination of any embodiment described above or below, for rare fine art, some shipments may produce some stress that may not be physically shown until sometime in the future so small changes in the quality metric could produce long-term manifested reductions in art value, the exemplary inventive computer-based system of the present disclosure may be configured to utilize a percent remaining value curve that can be based on determinations of both the short- and long-term valuation effects of shocks and vibration as shown in an exemplary graph of FIG. 19.

Figure 19:
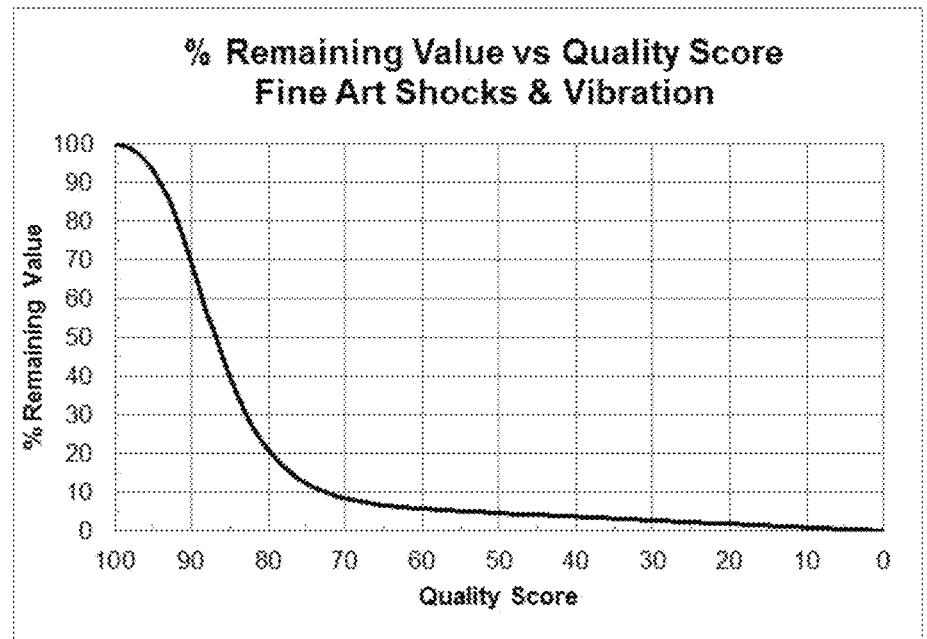

From the graph of FIG. 19, the relative sensitivity of this fine art to shocks and vibration for this example is shown. At the exemplary quality metric of 80, the percent remaining value is reduced to 20% of the stated value before transport.

In FIG. 4 shows a sample of a database that could be used in computing quality metric premiums as depicted in FIG. 3 step 330. Historical cargo journey data along with their associated scores can be compiled for application in the pricing model. In some embodiments and, optionally, in combination of any embodiment described above or below, for each cargo shipment of a specific product, peanuts, for example, the data fields may be: source, destination, date shipped, date arrived, shipper, container type, shipment value, and resulting quality metric. This data provides a quantitative record of experience that may be processed by the exemplary inventive computer-based system of the present disclosure to give users a basis for the cargo transport quality shortfall administration such as developing quality metric shortfall and property premiums.

Figure 5:
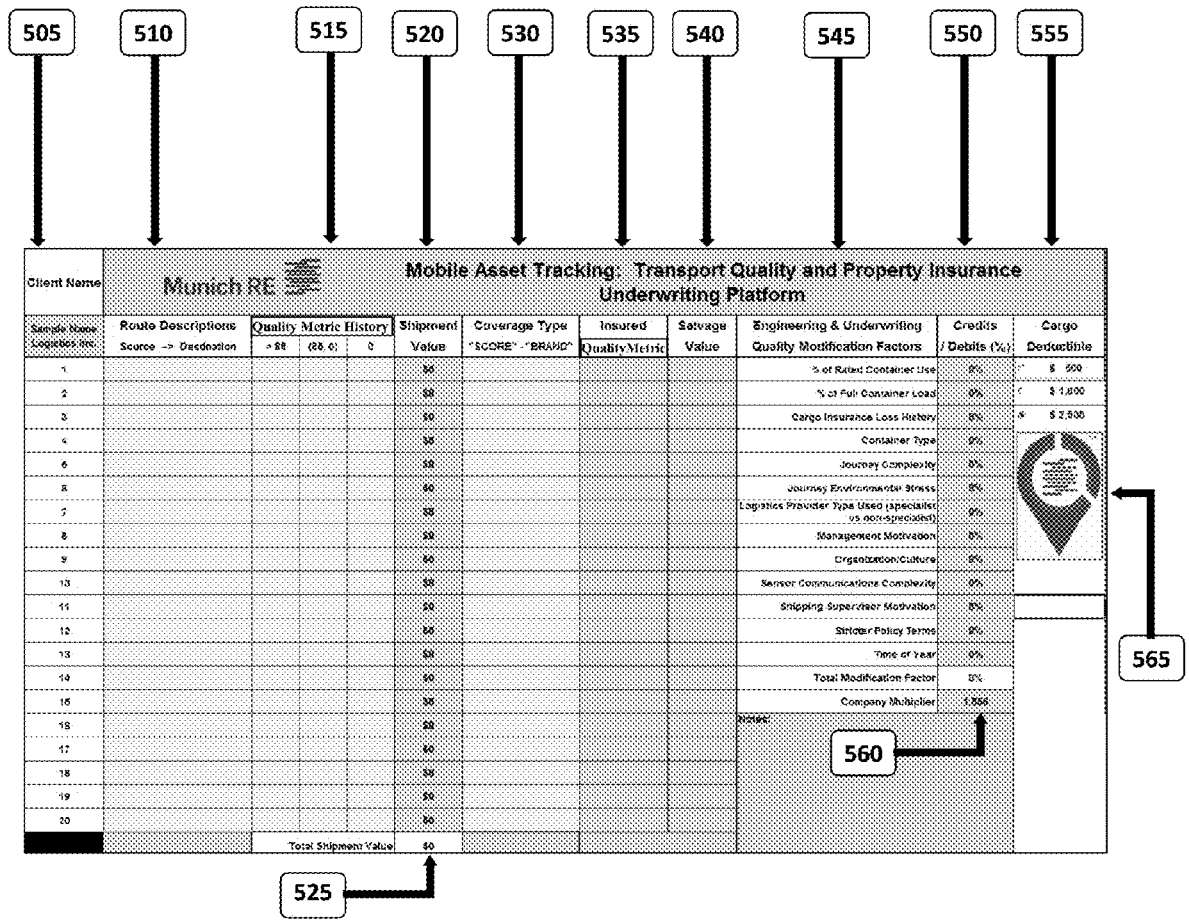
FIG. 5 shows a snapshot of a graphical user interface programmed to demonstrate an illustrative model how the data is compiled and integrated in accordance with at least some embodiments of the present disclosure.

In FIG. 5, the exemplary inventive cargo transport quality shortfall administration platform shown in FIG. 3 step 340 is presented. At step 505, the underwriter enters the client name since the analysis is targeted at a specific client and their transport details; or the exemplary inventive computer-based system of the present disclosure may be configured to automatically populate this information from data that may be obtained, in the past and/or in real-time, from a client's computer system and/or any other suitable computer source. Then in 510 the journey source-destination pair from a fixed list is selected for each shipment planned over a given period, for example one year. The source and destination pairs may be the results of a risk analysis of the historical data that groups detailed destinations into common sources and destinations that share common risk and geographic characteristics. Once the Source-Destination choice is recorded, at step 515, the historical fraction of shipments where the quality metric lies within three ranges: >85, (85-10), and 0 are displayed. These ranges are for illustrative purpose only and other suitable ranges may be applied. The percentages give the underwriter the historical quality metric experience associated with shipping between the source and destination. In some embodiments and, optionally, in combination of any embodiment described above or below, if no historical data is available the underwriter or analyst can enter their expert opinion on the probability of achieving a given score. In some embodiments and, optionally, in combination of any embodiment described above or below, even if historical data exists, the underwriter can overwrite the given percentages to customize the historical data to the situation being underwritten and priced.

At step 520, the underwriter adds the insured shipment value; or the exemplary inventive computer-based system of the present disclosure may be configured to automatically populate this information from data that may be obtained, in the past and/or in real-time, from a client's computer system and/or any other suitable computer source. This value represents the insurance financial exposure for shipment and the total insured or shipment value is listed at step 525.

At step 530 the underwriter selects the particular type of quality metric insurance coverage desired: "SCORE" or "BRAND"; or the exemplary inventive computer-based system of the present disclosure may be configured to automatically populate this information from data that may be obtained, in the past and/or in real-time, from a client's computer system and/or any other suitable computer source. For example, the SCORE coverage identifies that if the journey quality metric is below the insured quality metric, then the insured is paid the amount equal to the initial shipment value times the difference in economic percentages from the insured score and actual score, illustrated an equation (9):

Shipment value*(% Economic Value at Insured score−% Economic Value at Actual Score)     (9).

Figure 20:
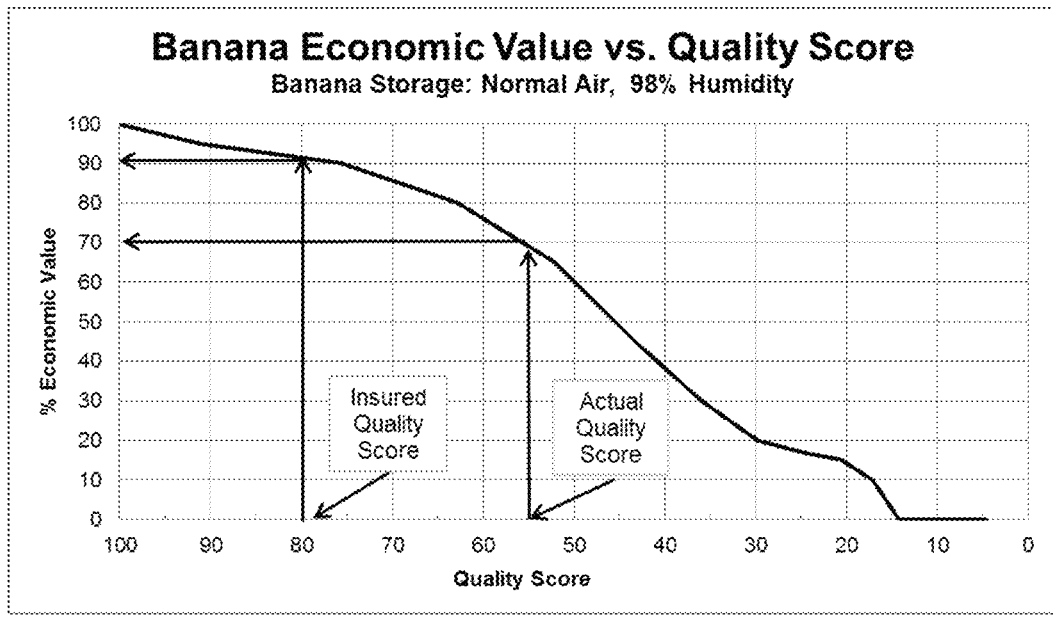

As an example, using the quality metric to economic value plot shown in an exemplary graph of FIG. 13. Suppose the cargo's insured quality metric for a given journey was 80 and the actual quality metric was 55. The exemplary graph of FIG. 20 shows the two scores on the horizontal axis the resulting % economic loss values on the vertical axis. The economic value of the insured quality metric of 80 is 90% and the % economic value of the actual score is 70%. The claim amount for a $100,000 cargo shipment would be $100,000*(90%−70%) or $20,000.

In the BRAND coverage option, the quality metric to economic value curve is not used. BRAND coverage assumes that the cargo has lost all or most its economic value if the quality metric falls below the insured selected score. The claims payment is a binary calculation as shown in Table 3.

TABLE 3

| Actual Quality | ≥Insured Quality Metric<br>Action: No claim<br><Insured Quality Metric<br>Action: Claim = Shipment Value − Salvage Value |
|---|---|

At step 535 the underwriter enters the insured provided quality metric for which they desire protection; or the exemplary inventive computer-based system of the present disclosure may be configured to automatically populate this information from data that may be obtained, in the past and/or in real-time, from any suitable computer source. This score choice may be solely the responsibility of the insured and may reflect their risk acceptance and their confidence in the shipper and container for a given journey.

In some embodiments and, optionally, in combination of any embodiment described above or below, there is no deductible explicitly used in this type of coverage. In some embodiments and, optionally, in combination of any embodiment described above or below, the insured essentially chooses a deductible by selecting the insured quality metric. In some embodiments and, optionally, in combination of any embodiment described above or below, for SCORE coverage, the decrease in economic value from 100% to the value at the insured quality metric is the insured deductible amount. In some embodiments and, optionally, in combination of any embodiment described above or below, for BRAND coverage, the lower the insured quality metric, the insured accepts a greater loss of perceived value even though there is no economic loss unless the actual score is less than the insured score.

At step 540 the underwriter adds the shipment's salvage value if the shipment is insured with BRAND coverage; or the exemplary inventive computer-based system of the present disclosure may be configured to automatically populate this information from data that may be obtained, in the past and/or in real-time, from any suitable computer source.

At step 545 the engineering and underwriting risk modification factors are listed. Risk modification factors are common in insurance underwriting and serve to customize a given risk relative to the more general historical data produced premium. In the case of pricing cargo transport quality shortfall, the specific factors listed in this step reflect the unique risk characteristics and they may be different in other embodiments to reflect the risk modification factors that pertain to a specific type of cargo.

At step 550 the underwriter supplies their subjective insights to pricing the risk by selecting the credits and debits to the model computed premium associated with some or all the modification factors listed; or the exemplary inventive computer-based system of the present disclosure may be configured to automatically populate this information from data that may be obtained, in the past and/or in real-time, from a client's computer system and/or any other suitable computer source. A credit (+%) decreases the premium and a debit (−%) increases the policy premium. The summation of the risk modification factor percentages is multiplied by the model computed premium to customize the premium computed from the historical data to the specific characteristics of the policy being underwritten and priced.

At step 555 the underwriter enters the insured's desired deductible for standard property insurance; or the exemplary inventive computer-based system of the present disclosure may be configured to automatically populate this information from data that may be obtained, in the past and/or in real-time, from any suitable computer source. Standard cargo transport rates and deductibles may be included in the calculations with the property premiums computed using the selected deductible and shipment values. In some embodiments and, optionally, in combination of any embodiment described above or below, these calculations may apply standard actuarial methods that utilize company-specific rates. In some embodiments and, optionally, in combination of any embodiment described above or below, they may be included in the quality shortfall premium pricing to simply provide clients a combined property and transport quality insurance package if desired.

As referenced herein, the term "quality insurance" means any insurance product/service that includes, builds upon and/or is derived from any principle detailed in the present description.

As referenced herein, the term "quality determination" means any determination that includes, builds upon and/or is derived from any principle detailed in the present description related to the storage and transport of goods (e.g., perishable goods, antiques, pharmaceuticals, automobile parts, computer parts, etc.), including, without limitation, the quality insurance.

At step 560, the underwriter enters a multiplier that transforms the loss cost-based Monte Carlo results into the full policy premium value; or the exemplary inventive computer-based system of the present disclosure may be configured to automatically populate this information from data that may be obtained, in the past and/or in real-time, from any suitable computer source. The multiplier reflects the additional charges required covering profit, expenses, claims administration, and other similar costs associated with the administration of the quality shortfall.

At step 565, the underwriter executes the exemplary cargo transport shortfall administration platform which may run the Monte Carlo premium computation.

Figure 6:
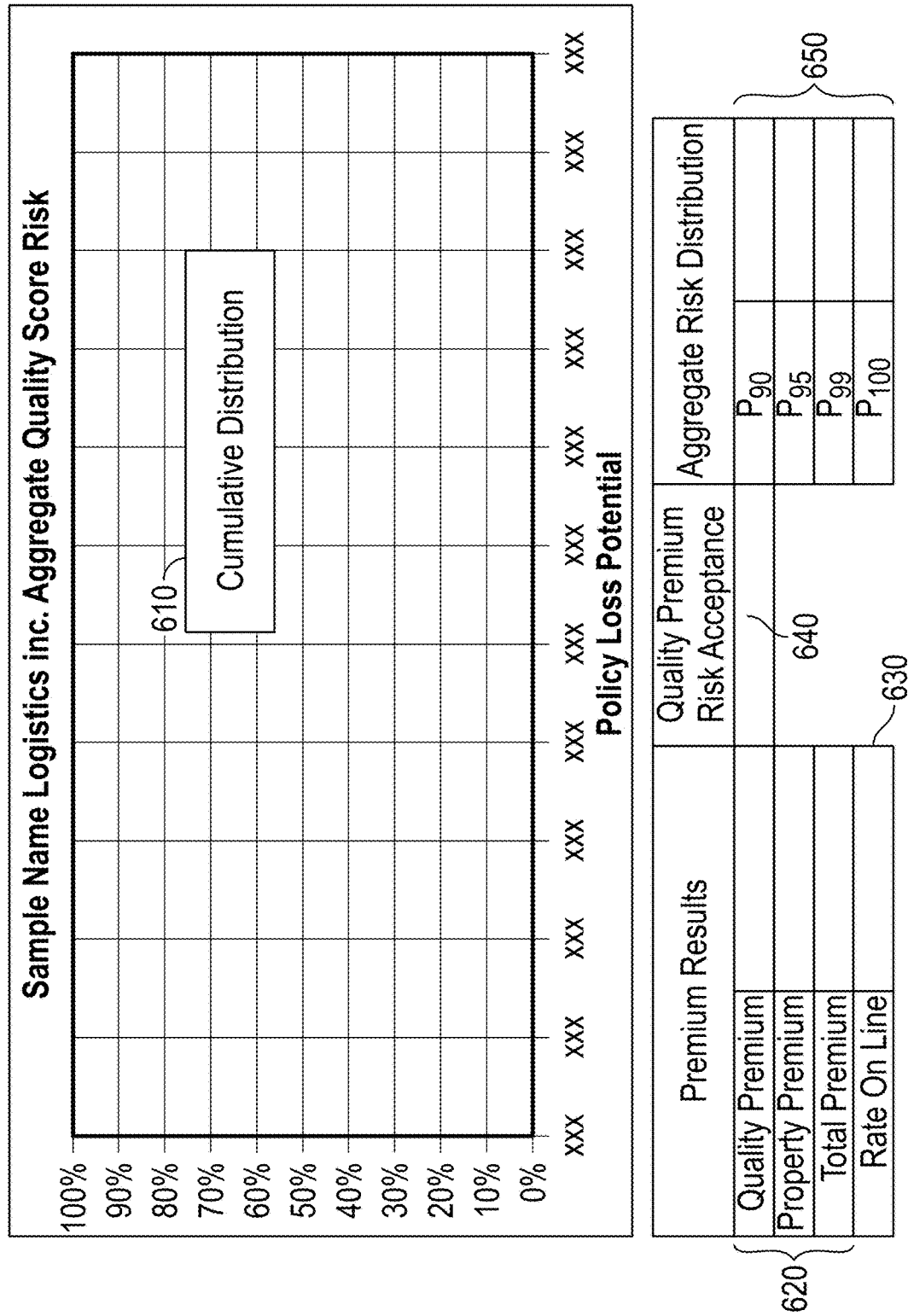
FIG. 6 shows certain aspects in accordance with at least some embodiments of the present disclosure.

The illustrative output of the Monte Carlo calculation is shown in FIG. 6. At step 610 the total, aggregate risk distribution is shown for the underwriter's review. It visually shows the total range of outcomes on the horizontal axis (x) and their associated probabilities on the vertical axis (y). It is displayed as a cumulative probability distribution function which indicates for any given point on the curve denoted as (x, y), there is a 'y' probability, that the actual outcome will be 'x' or less. And also, there is (1−y)' probability that the losses will be greater than 'x'.

At step 620, the average quality premium and the shipment value and deductible-based property premium values are listed. This enables the underwriter to price the quality shortfall coverage, property coverage, and both together. The dot on the curve of the distribution shown in step 610 also visually shows the average quality premium.

At step 630, the model computes the rate on line, a standard industry metric by dividing the total premium charges by the total shipment value as shown in FIG. 5 step 525. Other indicators may be used instead of, or in addition to the rate on line metric. Moreover, additional standard insurances in addition to property insurance could also be included with the quality metric insurance in other embodiments of this invention.

At step 640, the model computes the percentage of the quality shortfall policy's risk exposure or loss potential that is accepted by the underwriter. The percentage indicates the probability that the losses could be greater than the quality shortfall premium shown in step 620.

At step 650, the four specific loss potential percentile values are listed. These values can help the underwriter finalize the premium charges and are also useful for discussions related to program or policy reinsurance issues.

As an example of how the exemplary inventive computer-based system of the present disclosure may be configured to administer the transport quality shortfall premium, consider the transport of high value wines from France to various locations around the world by a given shipper. As shown in FIG. 3, the inputs to the underwriting and pricing model, given the sensor supplied time-series data, may be 1) the environmental data to quality metric function, 2) the percent remaining value versus quality metric function, and historical data for shipments with their associated metrics and cargo transport attributes.

Examples of the 1) and 2) have been presented in the graphs of FIGS. 15 and 16 respectively and a sample of the available historical data that may be used is shown in FIG. 6.

In some embodiments and, optionally, in combination of any embodiment described above or below, an exemplary quality metric can be computed for each sensor-based wine storage unit and the temperature degree days (>15° C.) can be computed to produce a shipment's quality metric from the above plot.

Based on this curve and the anticipated sophistication of the final buyer of the wine, the shipper, wine owner and insurer agree on the percent remaining value as a function of the exemplary quality metric.

Figure 7:
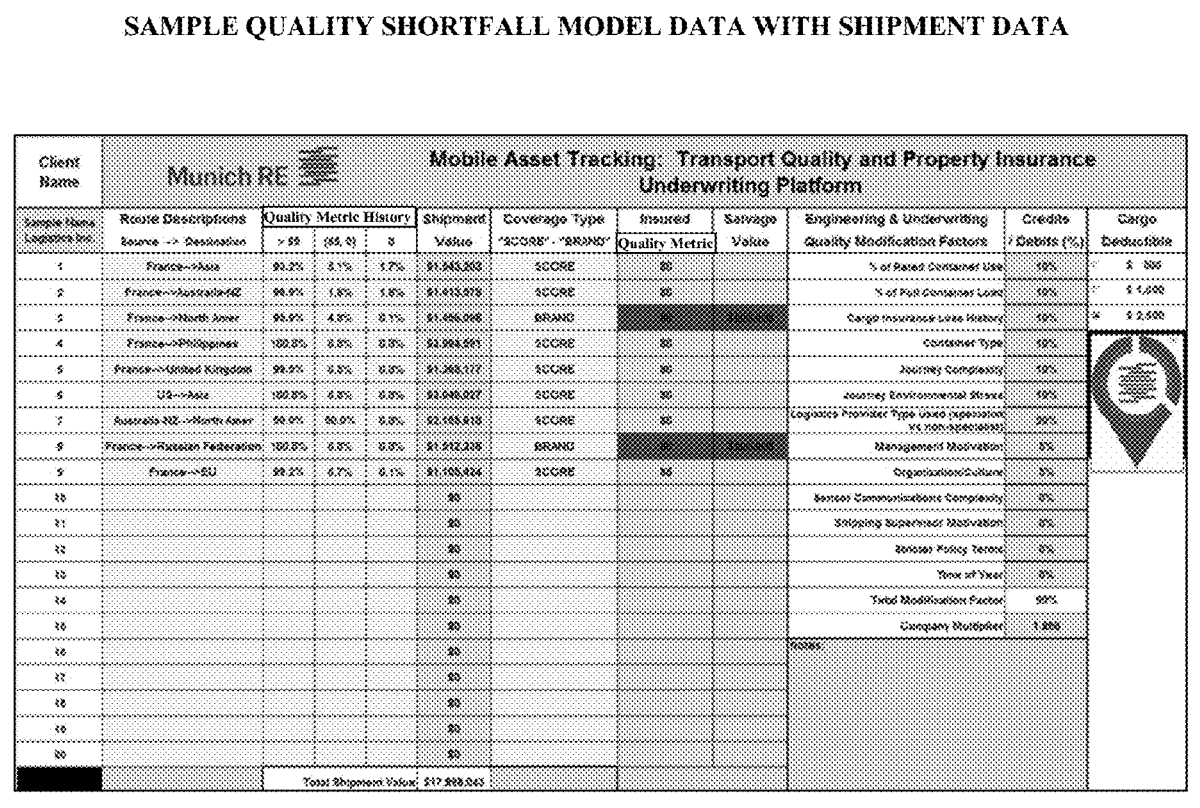

To underwrite and price specific cargo shipments, the shipper may supply the necessary shipment data as discussed in FIG. 3 step 330. With this information, the exemplary inventive computer-based system of the present disclosure may be configured to execute the pricing model. At this point the pricing model contains the information as shown in FIG. 7.

The Route Descriptions, Quality Metric Historical performance, Shipment Values, the Coverage Type, Insured Quality metrics and two (2) of the nine (9) shipments require brand coverage for which the wine salvage values are also a part of the shipper supplied data.

At this point, the underwriter enters any risk modification factors to customize the pricing and the Company Multiplier, in this case set to 1.856 to cover expenses, profit, etc.

Figure 8:
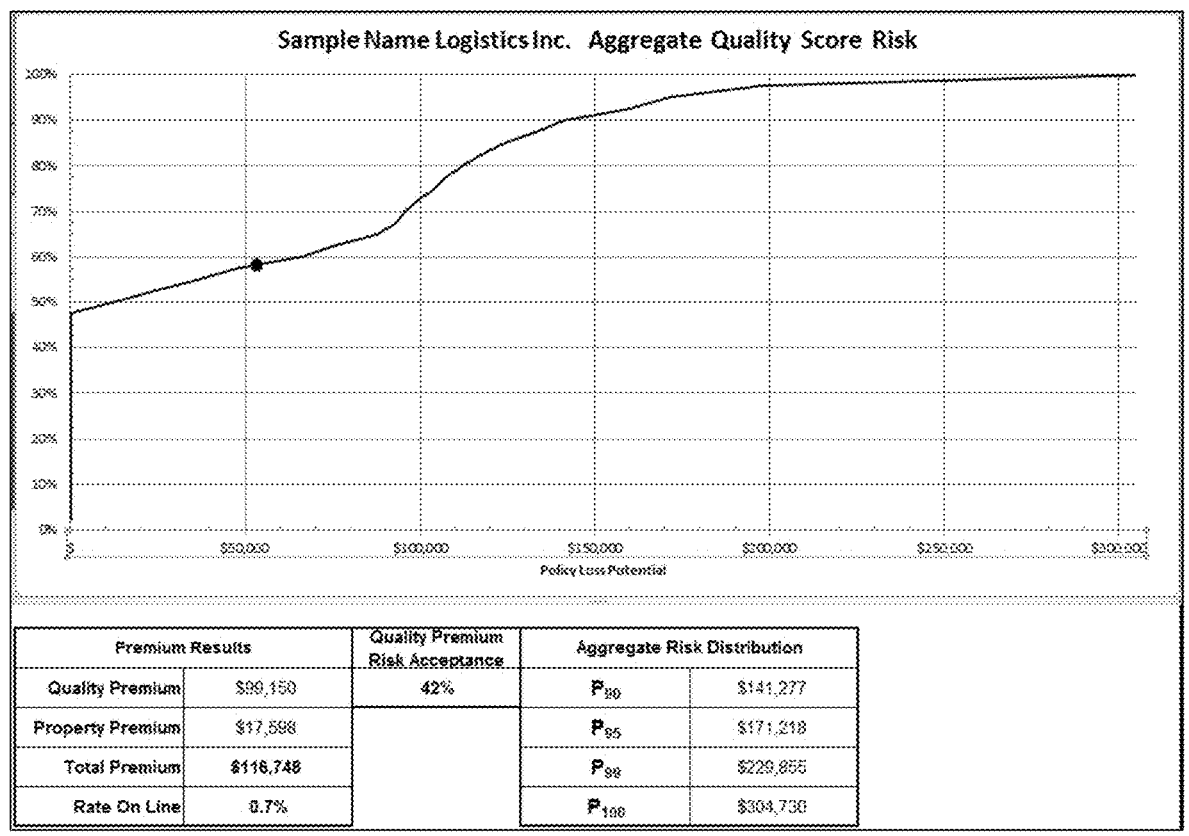
FIGS. 8-10 show certain aspects in accordance with at least some embodiments of the present disclosure.

After selecting the desired property insurance deductible by clicking on the icon, the model is run to output the premium calculations as shown in FIG. 8.

In FIG. 8, the Aggregate Risk Curve shows the underwriter the full range of loss potentials. The dot refers to the location on the curve of the "Quality Premium" listed as the average premium. The "Property Premium" and the sum, "Total Premium" are also listed. The "Rate on Line" is the "Total Premium" divided by the "Total Shipment Value" listed in FIG. 7. The "Quality Premium Risk Acceptance" value refers to a probability range from the vertical location of the dot on the curve to 100%. It describes how much risk the underwriter is accepting it they use the "Quality Premium" as listed. The "Quality Premium" is the average value of the "Aggregate Risk Distribution" shown in the plot. If the underwriter applies the listed $99,150, there is a 42% chance the loss potential could be larger than this value.

The "Aggregate Risk Distribution" percentile values listed given some additional quantitative information of loss potential to assist the underwriter to deciding on the proper premium charges for this policy. The information on this part of the risk model is designed to assist underwriters in this decision-making.

In another embodiment of this invention, fishing ships are dispersed from a harbor on a several day mission to fish and return to a common unloading station. Each ship has a different storage capacity, environmental cooling capability, and speed.

At the end of the fishing period, the ships transport their delicate cargo back to the dock where they are staged to get to the dock without interference from the other vessels. As time advances, the high market value fish deteriorate to such an extent that they need to be re-purposed as fish oil stock at a lower market value. In some embodiments and, optionally, in combination of any embodiment described above or below, the exemplary inventive computer-based system of the present disclosure may be configured with relationships between environmental conditions and fish quality and fish value.

Environmental sensors are applied to each ship's storage hold to capture the key parameters to measure fish quality in real time and GPS sensors to capture vessel location and speed. The quality shortfall insurance may be applied to the off-loaded market value of the fleet's total catch. The exemplary inventive computer-based system of the present disclosure may be configured to execute the quality shortfall administration reflective of an insurance that may provide an insured floor for the total revenue from a catch.

With the environmental data to quality metric and the quality metric to remaining value functions known, the transport quality and property administration platform model shown in FIG. 5 may be used. Each vessel's catch (shipment value), the type of coverage and an insured quality metric are entered. The historical performance of each ship is entered in the "Quality Metric History." If known, otherwise it is entered from the underwriter's experience.

Since there is a limitation in dock space, the vessel may wait in a queue before they can unload and during time, the catch value can erode. Based on each vessel's catch tonnage, location, and speed an optimization program is run to ensure each vessel arrives at the dock without interference and the total catch revenue is maximized.

Figure 9:
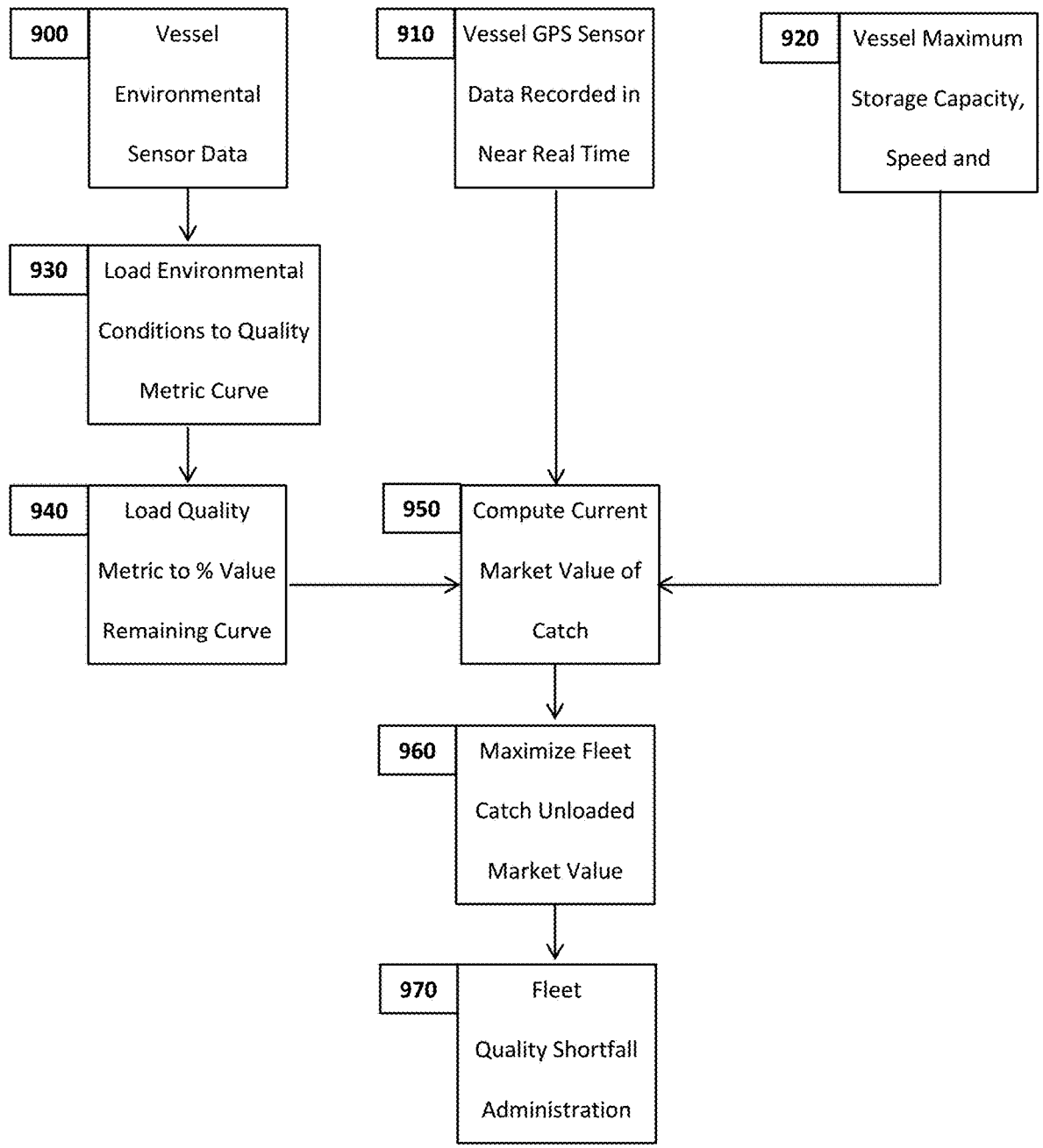

The elements of this embodiment are presented in FIG. 9. In step 900 vessel installed environmental sensors may record and transmit, in near real time to a central server, without limitation, catch tonnage, temperatures, nitrogen content, etc.

At step 910, GPS and vessel-specific ID codes are transmitted in near real time to a central server.

At Step 920, the central server also loads for each vessel (or vessel ID) its maximum storage capacity, maximum sustainable speed, and refrigeration limits.

At step 930, for each vessel, the environmental conditions to quality metric function are loaded to the server.

At step 940, for each vessel, the quality metric to percent value remaining function is loaded to the server.

At step 950, given each vessel's current catch, % remaining value results and distance from unloading, compute the current vessel and fleet level market value At step 960, run an optimization model to provide each vessel's speed to arrive at dock to avoid waiting and to maximize the fleet level market value.

At step 970, load the vessel specific data into the underwriting and pricing model to compute policy costs for cargo property insurance and insurance for fleet-level quality shortfall.

Figure 10:
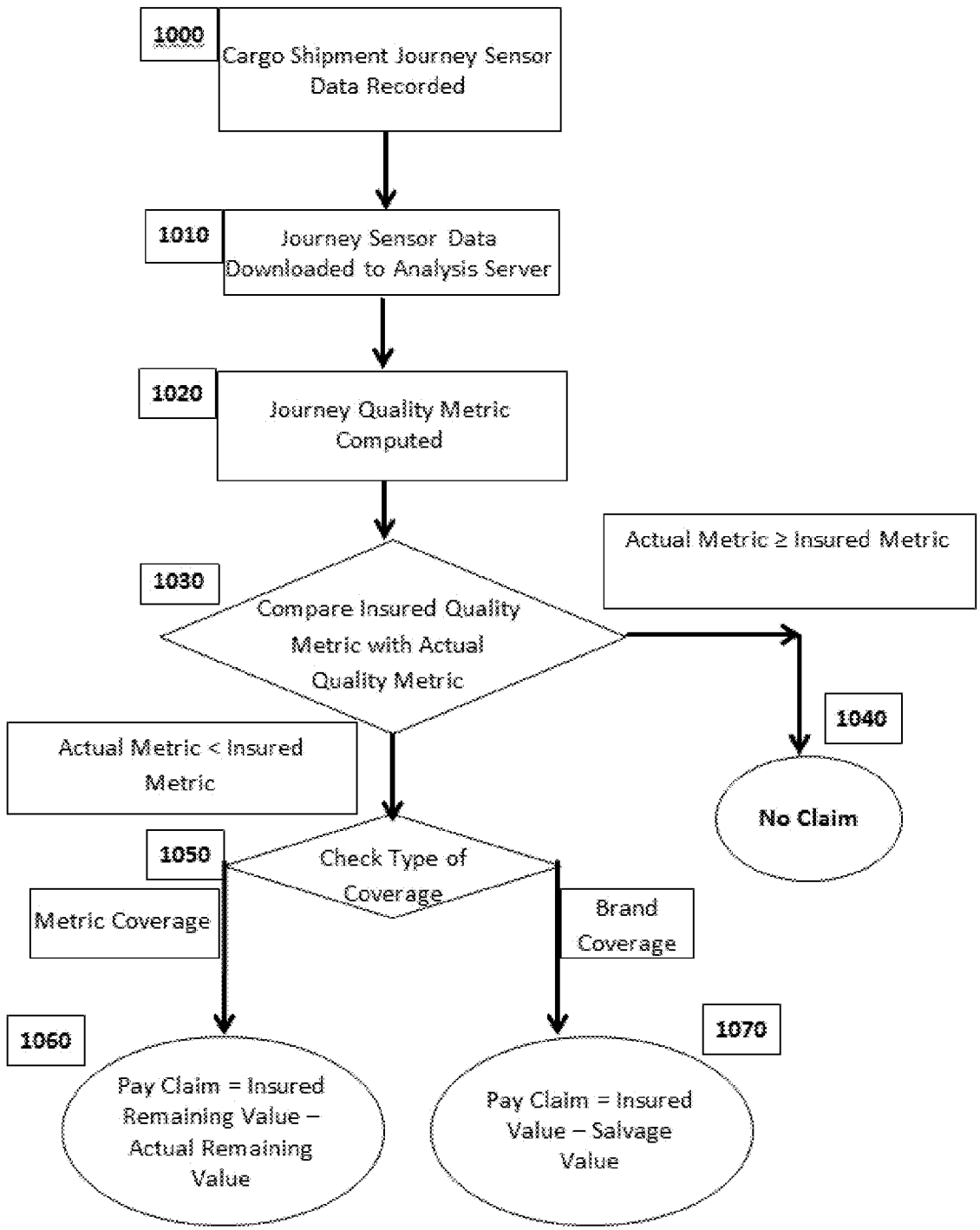

FIG. 10 is an illustrative process flow representation as to how the inventive cargo transport quality shortfall administration may be handled throughout the lifecycle.

At step 1000, cargo shipment data is cargo transport environmental condition data is recorded for the total duration of the transport journey via land, sea, air, or with any combination. One or more sensors are attached to the cargo container to record and store environmental conditions as a function of time. The sensors are pre-programmed to record environmental conditions at the desired sampling rate that can vary depending on the unique requirements of the shipper and the cargo's sensitivity to adverse conditions.

For example, if the cargo is adversely affected by temperatures exceeding a given range for more than one hour, the sampling rate may be set at 5-minute intervals to provide the capability to signal the shipper and/or the insurer that actions need to be taken quickly to prevent a loss. As another example, if fine art truck shipment is sensitive to shocks, the sampling rate could be set to 1 minute or less to warn all interested parties that road's surface and/or the truck speed (computed from a GPS sensor) are excessive and to direct the drive to take appropriate action. For longer, multi-week journeys traveling by ship for example, sampling rates may be set to one hour or longer to conserve sensor battery life. In general, the selected sampling rate may be based at least in part on one or more of cost of each sensor, performance characteristics, battery life, and/or data storage.

In step 1010, sensor stored raw environmental data may be periodically transmitted to a central location or completely stored on the sensors and downloaded once at the end of the journey. Data transmitting frequency may dynamically vary based at least in part on suitable economic characteristics, technical requirements, battery life, and/or data storage. If a shipment is highly time sensitive, then the transmission interval could be continuous via cellular networks as in the case of temperature monitoring for valuable pharmaceuticals. The data may be collected for the complete journey: from shipment source to shipment destination.

In step 1020, the time-based environmental data is used to compute a journey quality metric. There may be separate metrics or a combined quality metric, for example, for temperature effects, for humidity effects, and/or for acceleration (shock) effects. In each case, the time-based data is processed based on an exemplary mathematical algorithm that computes a quality metric representing the overall environmental effects on the inherent quality of the cargo.

In step 1030, the transport quality metric is compared to the insured quality metric. If the quality metric is greater than the insured quality metric, then in step 1040, there is no claim and the contract for this journey is closed.

If the actual quality metric is less than the insured quality metric, then assuming the policy's terms and conditions are met the coverage applies. Next in step 1050, the type of coverage purchased by the insured must be identified.

If the coverage type is "Score", then the claim amount is computed in step 1060 as the insured remaining value—the actual remaining value and the contract for the journey ends.

If the coverage type is "Brand", then the claim amount is computed in step 1070 as the insured value—the salvage value and the contract for the journey ends.

Figure 23:
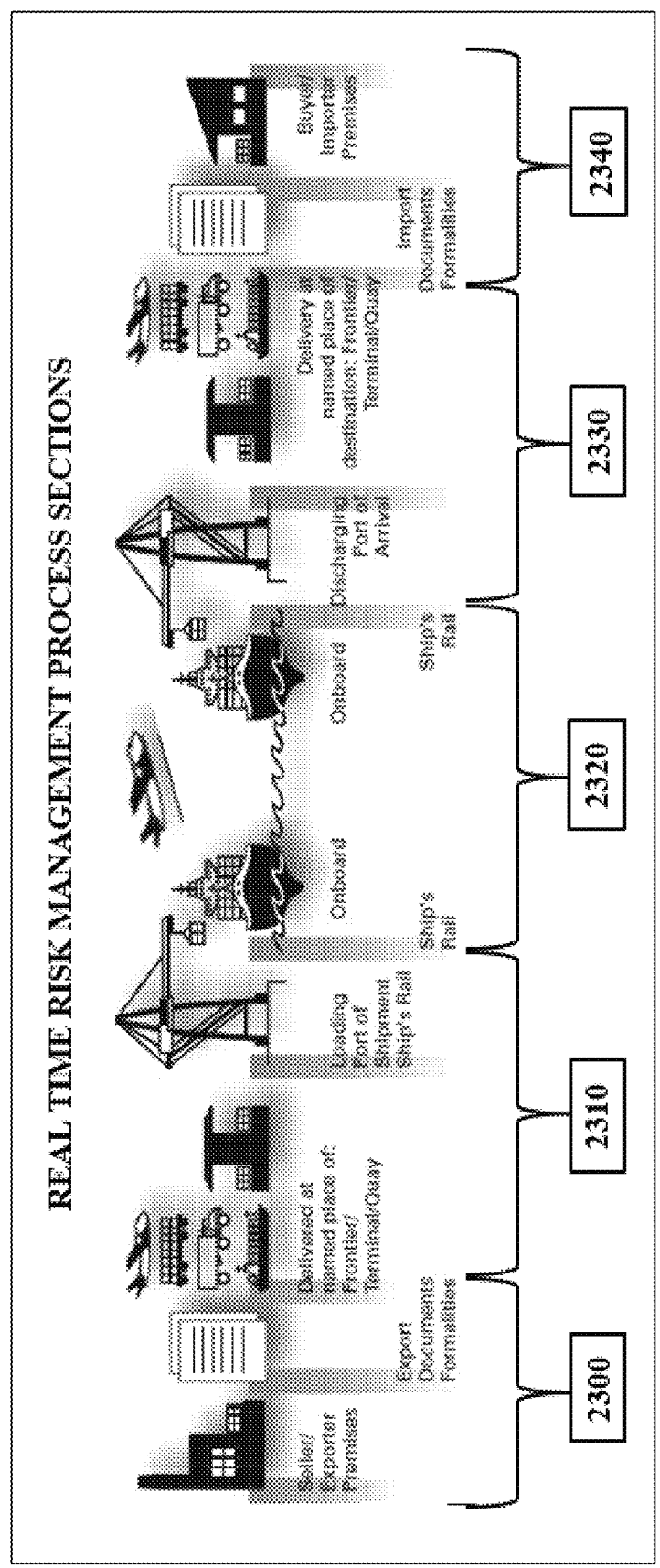
FIG. 23 shows an exemplary process flow for certain aspects of at least some embodiments of the present disclosure.

In some embodiments and, optionally, in combination of any embodiment described above or below, the exemplary inventive computer-based system of the present disclosure, executing the exemplary inventive cargo quality shortfall administration software, may be configured to dynamically manage, in real-time, various types of activities that a cargo shipment may experience throughout the lifecycle of policy coverage as illustrated in FIG. 23. For example, at step 2300, the cargo leaves the seller/origin location via truck or rail car and may travel to a cargo hub for placement on board another conveyance with or without further manipulation or consolidation of additional cargoes. At step 2310, the cargo leaves the cargo hub for delivery to the main port of export. For example, this could be airport, seaport or truck terminal and cargo may be further manipulated to better fit the cargo carrying conveyance, for example a 20' Ocean Container, a Unit Load Device (ULD) airfreight container, or a 53-foot truck trailer. At step 2320, the illustrative cargo is on its main carrying conveyance which could be via air, ground and/or ocean and the duration of transit could take between hours to over 30 days in time. At step 2330, the illustrative cargo is unloaded from its carrying conveyance at the destination place or port in reverse of the steps as outlined regarding step 2310. At step 2340, the illustrative cargo may be further deconsolidated and placed into different carrying conveyances for the final delivery to the buyer/importer. In this example, each leg of the journey may be carried out by different transporters each with their own limitations of liability and methods to record cargo condition. With most cargo transporters, typically, cargo condition is only recorded in writing on transport documents and only to record the physical condition of the goods by visual inspection. For example, typically, these records rarely reach the seller and/or buyer unless specifically requested by them after the journey has ended.

Figure 24A:
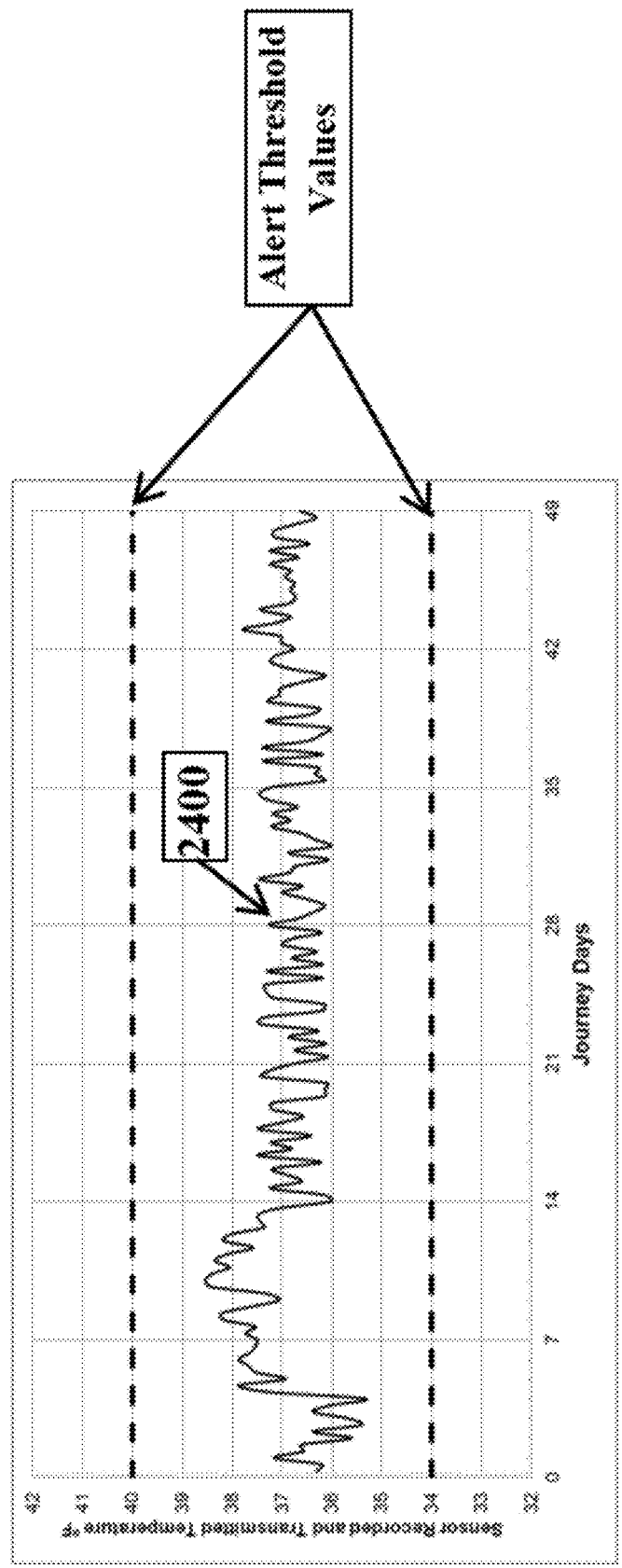
FIGS. 24A-24C show examples of sensor readings under normal and abnormal conditions requiring risk management remedial actions in accordance with at least some embodiments of the present disclosure.
Figure 24B:
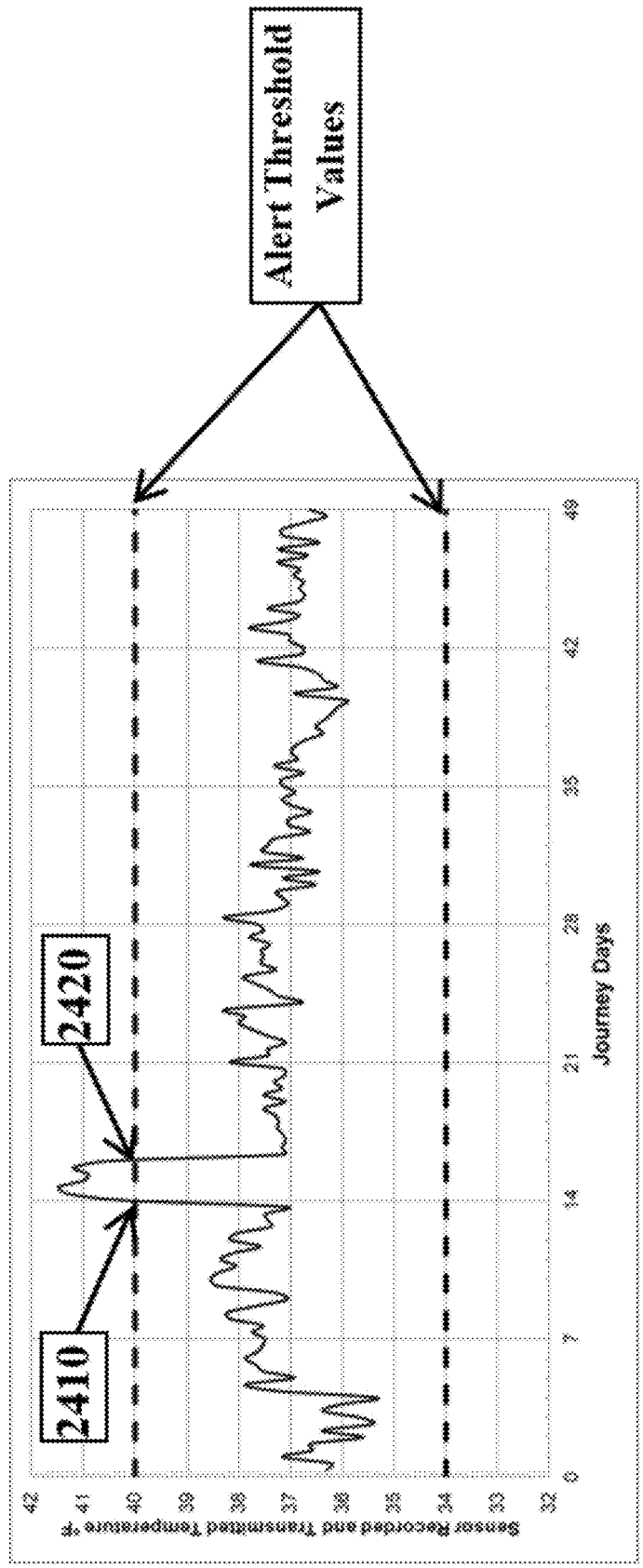
Figure 24C:
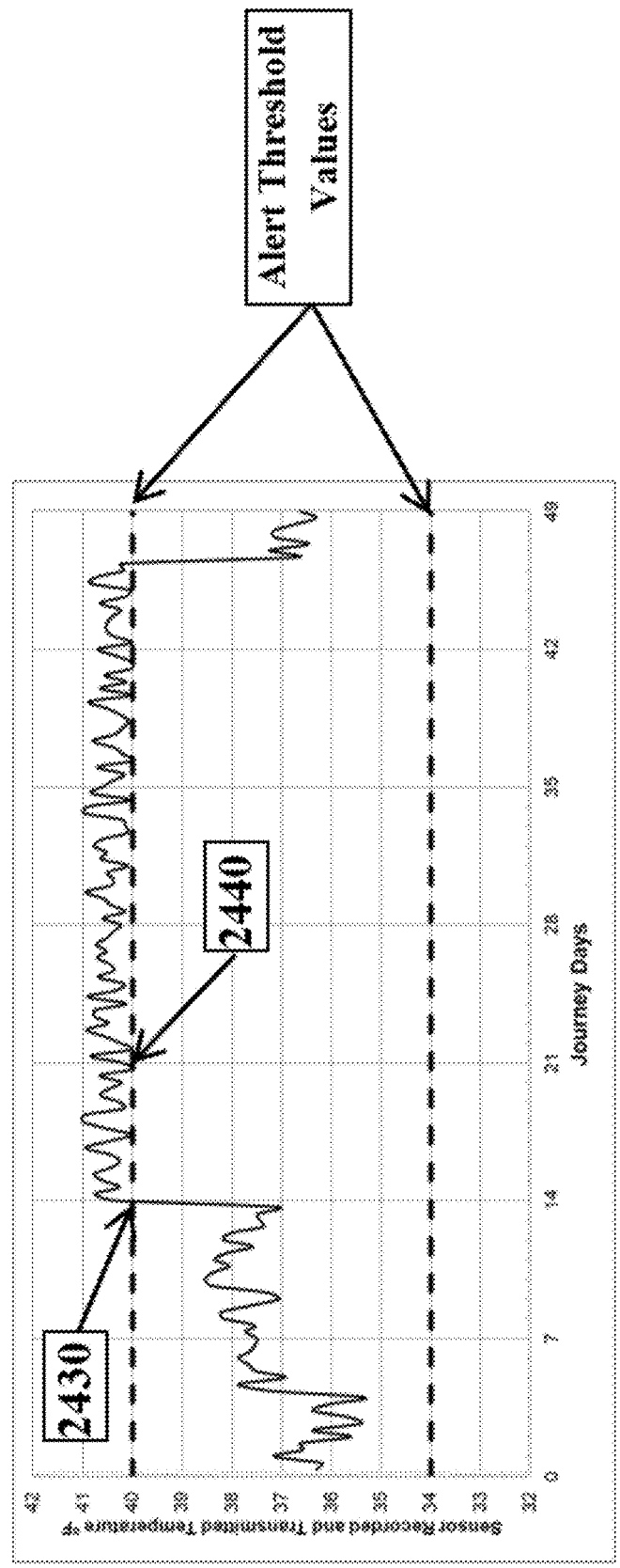
Figure 25:
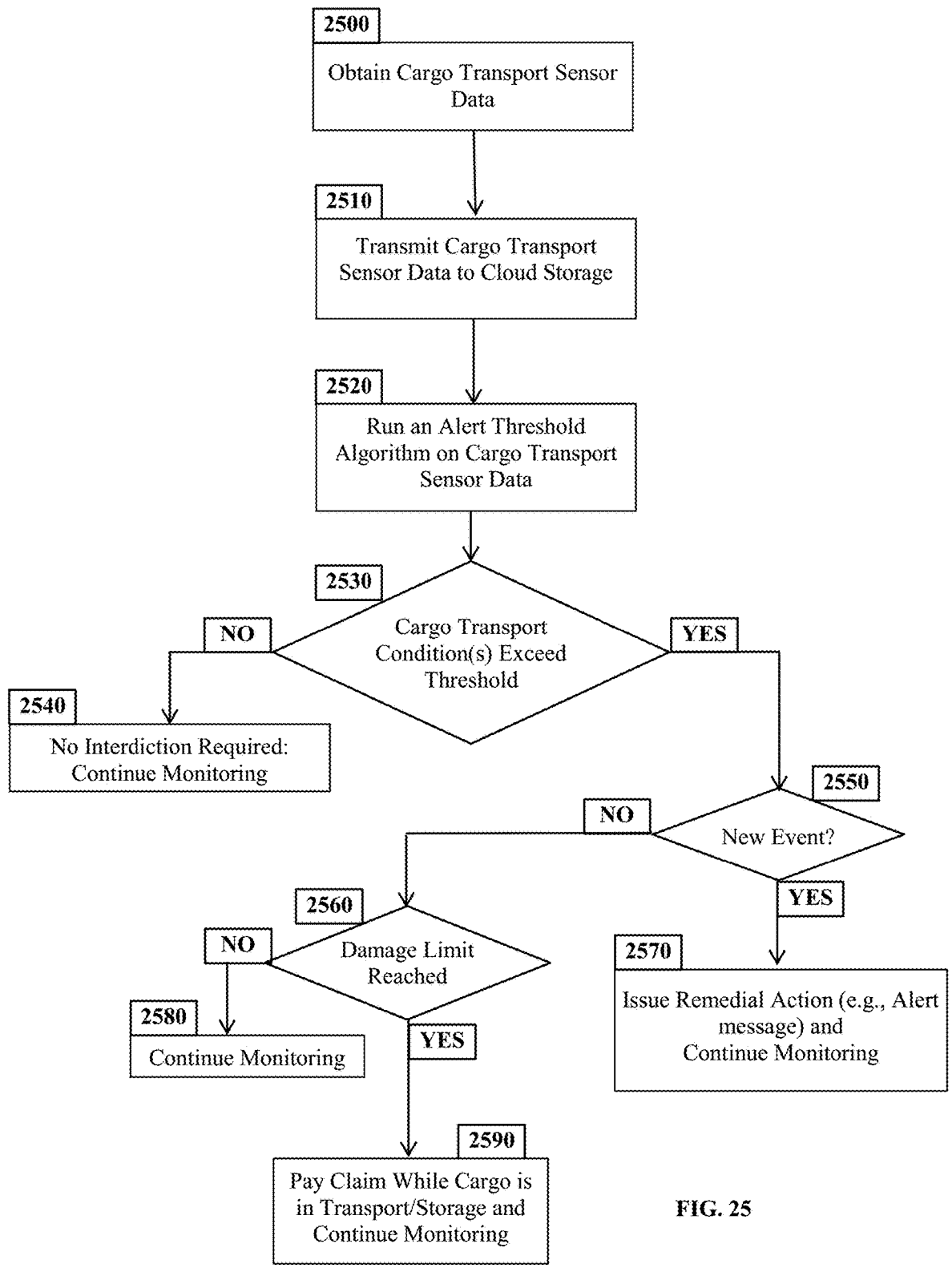
FIG. 25 shows an exemplary process flow for certain aspects of at least some embodiments of the present disclosure.

For example, FIGS. 24A-24C displays an exemplary environmental condition sensor time series data plot for a cargo temperature that shows graphically, for example, three risk management operational categories. FIG. 24A shows an exemplary plot of temperature vs. time. For example, the exemplary plot of FIG. 24A continues to grow as more temperature data is transmitted in time. For example, the dotted lines show the quality insurance policy-defined temperature threshold(s) that delineate when to generate an Alert from the normal operating region(s). For example, temperatures below or over the normal operating values signify abnormal operations and remedial actions may be warranted to correct them. For example, in the exemplary plot of FIG. 24A, the cargo transport and/or storage is operating within the insurance-defined threshold values so no remedial action is required.

For example, FIG. 24B shows an exemplary situation where the temperature has exceeded the Alert's threshold value at day 14. When this occurs, for example, the exemplary inventive computer-based system of the present disclosure, executing the exemplary inventive cargo quality shortfall administration software, may be configured to send via email, text, and/or phone one or more messages with one or more remedial actions to the policy holder, shipper and/or insurer (e.g., step 2410). For example, with the knowledge of a temperature issue, the shipper who is currently in custody and control of the shipment can investigate the reason(s) for the Alert and fix the problem. For example, in FIG. 24B, at step 2420, the shipper has located and fixed the issue (e.g., replaced a part, cleaned a filter, etc.) and the temperature returned to the normal operating range shown at step 2420. For example, the policy conditions of the exemplary quality insurance (e.g., Green, Yellow, or Red conditions of FIG. 21) show that no claim has occurred (Green condition) so only ongoing monitoring occurs as the cargo shipment continues to be transported through the sections described by FIG. 23.

FIG. 24C provides another example when the monitored cargo temperature exceeded the Alert's threshold value again on day 14 of the journey. For example, in such situation, the Alert message(s) and subsequent remedial actions were unable to correct the problem and the temperature remained in the Alert region for several weeks. In such example, based on the quality insurance policy's documented conditions, the cargo quality entered the Yellow condition region of FIG. 21 and a claim payment was activated at this time at step 2440. In some embodiments, the exemplary inventive computer-based system of the present disclosure, executing the exemplary inventive cargo quality shortfall administration software, may be configured to cause the payment of additional payment(s) up to the policy limit as time advances but at the time shown at step 2440, all interested parties have advanced knowledge of at least a partial loss and a payment is issued to the insured at this time while the cargo is still in transport and/or storage, as outlined in the exemplary quality insurance policy.

FIG. 24 illustrates an exemplary process flow that the exemplary inventive computer-based system of the present disclosure, executing the exemplary inventive cargo quality shortfall administration software, may be configured to administer cargo shipments undergoing journeys such as shown in FIG. 23. For example, at step 2500, one or more sensors of the present disclosure may be attached and/or included with the cargo to record cargo transport data (e.g., environment data, transport operational data, etc.) at particular sampling rates that are consistent with best practices for the particular insured cargo. At step 2510, this information is periodically transmitted to, for example, a cloud server for storage and ongoing analysis of the incoming data either in batch or near real time by a server running the exemplary inventive cargo quality shortfall administration software. At step 2520, the exemplary server, running the exemplary inventive cargo quality shortfall administration software, may apply the Alert and other predictive algorithms to the cargo transport sensor data stream to, for example without limitation, analyze current out-of-specification (abnormal) situation(s)/condition(s) to measure if a particular time-based situation/condition warrants one or more remedial action (e.g., a claim payment) and/or identify equipment deterioration trends and notify the appropriate maintenance personnel.

For example, at step 2530, the exemplary server, running the exemplary inventive cargo quality shortfall administration software, may check for any cargo shipments where the environmental condition(s) is/are outside of the Alert threshold values. For example, when the exemplary server, running the exemplary inventive cargo quality shortfall administration software, determines that the cargo transport sensor condition(s) is/are within normal operating ranges, then at step 2540, the exemplary inventive cargo quality shortfall administration software, waits for more time-based sensor data to add to the analysis and continues the monitoring.

For example, when the server, running exemplary inventive cargo quality shortfall administration software, determines that the current cargo transport sensor values are outside the normal operating range(s) of one or more Alert threshold values, the exemplary server, running the exemplary inventive cargo quality shortfall administration software, generates an Alert event at step 2550 and checks to see if there are previous events during particular times. In some embodiments, upon determining of the Alert event, the exemplary server, running the exemplary inventive cargo quality shortfall administration software, may send one or more Alert messages the interested parties and/or multifunctional sensors of the present disclosure when, for example:

1) the temperature exceeds Alert Threshold by 5° F. or
2) the temperature has exceeded the Alert threshold value for the past "x" time intervals.

For example, when the exemplary server, running the exemplary inventive cargo quality shortfall administration software, determines that the exceedance observed in Step 2530 is a new Alert event, in Step 2550, the exemplary server, running the exemplary inventive cargo quality shortfall administration software, may automatically issue one or more Alert messages (e.g., remedial instructions) to, for example without limitation, the interested parties and/or particular equipment (e.g., sensors, transport, storage, container) as defined, for example, in the quality insurance policy in step 2570. For example, when the exemplary server, running the exemplary inventive cargo quality shortfall administration software, determines that the Alert event is not a new event, then in step 2560, the exemplary server may perform further processing, such as checking whether the "Red", "Yellow", or "Green" criteria of FIG. 21 have been met, to determine which remedial action to pursue. For example, when at step 2560, the exemplary server, running the exemplary inventive cargo quality shortfall administration software, determines that a claim threshold value (Alert threshold value) has been reached then the server may cause a claim payment to be issued in step 2590 for the cargo's current loss of value while the cargo is still in transit (including while being stored during the transit). In some embodiments, the exemplary server, running the exemplary inventive cargo quality shortfall administration software, may cause additional payments to be issued at this step as time goes on when the continued monitoring if the cargo transport sensor data shows that, for example, the environmental conditions continue to remain outside the normal operating ranges. For example, when the exemplary server, running the exemplary inventive cargo quality shortfall administration software, determines that the damage limit, as defined by the quality insurance, has not been reached, the exemplary server continues to monitor to determine whether the previously applied remedial actions are having any effect on bringing the sensed environmental condition(s) back within normal operating limits.

In some embodiments and, optionally, in combination of any embodiment described above or below, the exemplary inventive computer-based system of the present disclosure, executing the exemplary inventive cargo quality shortfall administration software, may be configured to execute in one or more positive feedback loops by utilizing environments sensor data about cargo and/or transport to generate electronic remedial instruction(s), as exemplary remedial activity, that affect(s) or is/are designed to affect, in real-time, how the transport (e.g., vehicle, ship, plane, etc.), cargo storage (e.g., refrigerated container, etc.), or both behave/operate to reduce or eliminate the quality shortfall of the transported goods (e.g., perishable goods, antiques, auto parts, etc.). For example, electronic remedial instruction(s) may slow down the transport (e.g., reduce speed of the truck/ship) to reduce G-forces that the cargo may experience based on the received environmental sensor data related to the transported cargo. For example, electronic remedial instruction(s) may cause a change in the movement direction of the transport (e.g., set new GPS coordinates for ship) to avoid weather conditions that may detrimental affect the cargo's current condition. For example, electronic remedial instruction(s) may cause a change in the fan speed of a fan incorporated into the cargo container to increase the air circulation inside the cardo container when, for example, during the transport of grains the real-time received environmental sensor data is indicative of an increased level of $CO_2$. As examples detailed herein illustrate, the ability of the exemplary inventive computer-based system to perform or cause to perform the inventive remedial feedback loops improves the operation of (e.g., trucks, ships, containers, storage systems, etc.) by allowing them to maintain the quality of the transported cargo and/or minimize decrease in the quality of the cargo—making such physical cargo transport assets smarter.

In some embodiments and, optionally, in combination of any embodiment described above or below, the exemplary inventive computer-based system of the present disclosure, executing the exemplary inventive cargo quality shortfall administration software, may be configured to affect a compensation provided for any quality shortfall based on transport/shipper/insured's ability to allow the exemplary inventive computer-based system to perform or cause to perform the inventive remedial feedback loops.

In some embodiments and, optionally, in combination of any embodiment described above or below, the present disclosure may utilize several aspects of at least one of:
U.S. Pat. No. 8,195,484, entitled Insurance product, rating system and method;
U.S. Pat. No. 8,548,833, entitled Insurance product, rating system and method;
U.S. Pat. No. 8,554,588, entitled Insurance product, rating system and method;
U.S. Pat. No. 8,554,589, entitled Insurance product, rating system and method;
U.S. Pat. No. 8,595,036, entitled Insurance product, rating system and method;
U.S. Pat. No. 8,676,610, entitled Insurance product, rating system and method;
U.S. Pat. No. 8,719,059, entitled Insurance product, rating system and method;
U.S. Pat. No. 8,812,331, entitled Insurance product, rating and credit enhancement system and method for insuring project savings.

In some embodiments and, optionally, in combination of any embodiment described above or below, the exemplary inventive computer-based system of the present disclosure may be configured to utilize one or more mathematical functions of the aforementioned patents to transform obtained sensor recorded and stored data through cargo shipment containers to remaining economic shipment values for the inventive cargo transport shortage administration. Consequently, the aforementioned patents are incorporated by reference in their entirety for such specific purposes.

In some embodiments and, optionally, in combination of any embodiment described above or below, the aforementioned patents refer to "Savings" as tangible or intangible and include but are not limited to increased revenue; reduced operational expenses maintenance expenses and capital expenditures; increased production through-put; reduced energy consumption; reduced emissions; increased emission credits; etc.

In some embodiments and, optionally, in combination of any embodiment described above or below, the exemplary inventive computer-based system of the present disclosure, executing the exemplary inventive cargo quality shortfall administration software, may be configured to utilize 1) the received environmental sensor data, 2) the received operational cargo equipment data (including, without limitation, the telemetric data, and energy consumption data), and/or 3) the third party's data reflective of a lifespan of various cargo equipment under various environmental and/or operational conditions (e.g., equipment-specific historical data, current energy consumption data, breakdown frequency, etc.) to predict, in real time, cargo equipment health condition (e.g., when particular cargo equipment may need to be serviced and/or would break down) and use the cargo equipment health data as one of the inputs for automatically generating, in real time, the remedial inventive instruction(s) that would result in reducing or eliminating the cargo's quality shortfall. For example, the real-time remedial instruction may instruct the cargo transport to transfer cargo from a first refrigerated container to a second refrigerated container as soon as possible because the equipment health data for the first refrigerated container may predict an imminent failure of a condenser. For example, the real-time remedial instruction may instruct the cargo ship to come back to the departure port or another close-by port due to a prediction that the ship's engine needs to be immediately serviced to avoid the breakdown.

In some embodiments, the exemplary sensors of the present disclosure and their data as collected by a third party (party not affiliated with the cargo owner, storage provider, and/or transportation provider) can be utilized, via, for example without limitation, a blockchain implementation, to prove when a loss has occurred thereby allowing to track and/or assignment liability and/or improve subrogation against a party that may be negligent in causing the loss.

In some embodiments and, optionally, in combination of any embodiment described above or below, the at least some embodiments of the present disclosure utilize a network of multi-functional sensors; where, based at least in part on a quality insurance, each multi-functional sensor of the network of sensors is positioned in, positioned on, or positioned in a vicinity of at least one of: i) a transported cargo, where the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, ii) wirelessly transmit, via one or more communication modes, the cargo transport sensor data from the respective sensor to at least one server, iii) wirelessly receive, from the at least one server, via the one or more communication modes, one or more remedial instructions and store the one or more remedial instructions in a second memory location of the respective multi-functional sensor, and iv) cause the one or more remedial instructions to be implemented with one or more of: the at least one cargo container, the at least one cargo transport, and the at least one cargo storage; the at least one server, having cargo quality shortfall administration software stored on a non-transient computer readable medium; where the at least one server what is remotely located from the network of multi-functional sensors; where, upon execution of the cargo quality shortfall administration software, the at least one server is at least configured to: i) receive the cargo transport sensor data from the network of multi-functional sensors; ii) dynamically predict, based at least in part on the cargo transport sensor data, at least one current quality metric of the transported cargo, where the at least one current quality metric is representative of a predicted quality loss of the transported cargo from an original condition of the transported cargo at the at least one first geographic location; iii) dynamically determine, based at least in part on the at least one current quality metric of the transported cargo and a cargo-specific value remaining curve of the quality insurance, a current loss value of the transported cargo; iv) dynamically determine, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality insurance, a payout amount to an owner of the transported cargo to compensate the current loss value of the transported cargo without a physical inspection of the transported cargo, and 2) transmitting the one or more remedial instructions to one or more multi-functional sensors of the network of multi-functional sensors, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least some embodiments of the present disclosure provides a method, including at least the following steps of: installing a network of multi-functional sensors; where, based at least in part on a quality insurance, each multi-functional sensor of the network of sensors is positioned in, positioned on, or positioned in a vicinity of at least one of: i) a transported cargo, where the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, ii) wirelessly transmit, via one or more communication modes, the cargo transport sensor data from the respective sensor to at least one server, iii) wirelessly receive, from the at least one server, via the one or more communication modes, one or more remedial instructions and store the one or more remedial instructions in a second memory location of the respective multi-functional sensor, and iv) cause the one or more remedial instructions to be implemented with one or more of: the at least one cargo container, the at least one cargo transport, and the at least one cargo storage; receiving, by the at least one server, the cargo transport sensor data from the network of multi-functional sensors; where the at least one server is configured to execute cargo quality shortfall administration software stored on a non-transient computer readable medium associated with the at least one server; dynamically predicting, by the at least one server, based at least in part on the cargo transport sensor data, at least one current quality metric of the transported cargo, where the at least one current quality metric is representative of a predicted quality loss of the transported cargo from an original condition of the transported cargo at the at least one first geographic location; dynamically determining, by the at least one server, based at least in part on the at least one current quality metric of the transported cargo and a cargo-specific value remaining curve of the quality insurance, a current loss value of the transported cargo; dynamically determining, by the at least one server, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality insurance, a payout amount to an owner of the transported cargo to compensate the current loss value of the transported cargo without a physical inspection of the transported cargo, and 2) transmitting the one or more remedial instructions to one or more multi-functional sensors of the network of multi-functional sensors, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least some embodiments of the present disclosure utilize a network of multi-functional sensors; where, based at least in part on a quality insurance, each multi-functional sensor of the network of sensors is positioned in, positioned on, or positioned in a vicinity of at least one of: i) a transported cargo, where the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, ii) wirelessly transmit, via one or more communication modes, the cargo transport sensor data from the respective sensor to at least one server; the at least one server, having cargo quality shortfall administration software stored on a non-transient computer readable medium; where the at least one server what is remotely located from the network of multi-functional sensors; where, upon execution of the cargo quality shortfall administration software, the at least one server is at least configured to: i) receive the cargo transport sensor data from the network of multi-functional sensors; ii) dynamically predict, based at least in part on the cargo transport sensor data, at least one current quality metric of the transported cargo, where the at least one current quality metric is representative of a predicted quality loss of the transported cargo from an original condition of the transported cargo at the at least one first geographic location; iii) dynamically determine, based at least in part on the at least one current quality metric of the transported cargo and a cargo-specific value remaining curve of the quality insurance, a current loss value of the transported cargo; iv) dynamically determine, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality insurance, a payout amount to an owner of the transported cargo to compensate the current loss value of the transported cargo without a physical inspection of the transported cargo, and 2) transmitting the one or more remedial instructions, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least some embodiments of the present disclosure provides a method, including at least the following steps of: installing a network of multi-functional sensors; where, based at least in part on a quality insurance, each multi-functional sensor of the network of sensors is positioned in, positioned on, or positioned in a vicinity of at least one of: i) a transported cargo, wherein the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, and ii) wirelessly transmit, via one or more communication modes, the cargo transport sensor data from the respective sensor to at least one server; receiving, by the at least one server, the cargo transport sensor data from the network of multi-functional sensors; where the at least one server is configured to execute cargo quality shortfall administration software stored on a non-transient computer readable medium associated with the at least one server; dynamically predicting, by the at least one server, based at least in part on the cargo transport sensor data, at least one current quality metric of the transported cargo, where the at least one current quality metric is representative of a predicted quality loss of the transported cargo from an original condition of the transported cargo at the at least one first geographic location; dynamically determining, by the at least one server, based at least in part on the at least one current quality metric of the transported cargo and a cargo-specific value remaining curve of the quality insurance, a current loss value of the transported cargo; dynamically determining, by the at least one server, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality insurance, a payout amount to an owner of the transported cargo to compensate the current loss value of the transported cargo without a physical inspection of the transported cargo, and 2) transmitting the one or more remedial instructions, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least some embodiments of the present disclosure utilize a network of multi-functional sensors; where, based at least in part on a quality determination, each multi-functional sensor of the network of sensors is positioned in, positioned on, or positioned in a vicinity of at least one of: i) a transported cargo, where the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, ii) wirelessly transmit, via one or more communication modes, and the cargo transport sensor data from the respective sensor to at least one server; the at least one server, having cargo quality shortfall administration software stored on a non-transient computer readable medium; where the at least one server what is remotely located from the network of multi-functional sensors; where, upon execution of the cargo quality shortfall administration software, the at least one server is at least configured to: i) receive the cargo transport sensor data from the network of multi-functional sensors; ii) dynamically predict, based at least in part on the cargo transport sensor data, at least one current quality metric of the transported cargo, where the at least one current quality metric is representative of a predicted quality loss of the transported cargo from an original condition of the transported cargo at the at least one first geographic location; iii) dynamically determine, based at least in part on the at least one current quality metric of the transported cargo and a cargo-specific value remaining curve of the quality determination, a current loss value of the transported cargo; iv) dynamically determine, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality determination, a payout amount to an owner of the transported cargo to compensate the current loss value of the transported cargo without a physical inspection of the transported cargo, and 2) transmitting the one or more remedial instructions, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least some embodiments of the present disclosure provides a method, including at least the following steps of: installing a network of multi-functional sensors; where, based at least in part on a quality determination, each multi-functional sensor of the network of sensors is positioned in, positioned on, or positioned in a vicinity of at least one of: i) a transported cargo, wherein the transported cargo is a cargo that meets at least one of the following conditions: 1) a transported condition in which the transported cargo is transported from at least one first geographic location to at least one second geographic location by at least one cargo transport, or 2) a stored condition in which the transported cargo is being stored in at least one cargo storage while the transported cargo is transported from the at least one first geographic location to the at least one second geographic location, or ii) at least one cargo container containing the transported cargo; where each multi-functional sensor of the network of multi-functional sensors is configured to: i) measure at least one transport-related condition, at least one cargo-related condition, or both, to form cargo transport sensor data and store the cargo transport sensor data in a first memory location of a respective multi-functional sensor, and ii) wirelessly transmit, via one or more communication modes, the cargo transport sensor data from the respective sensor to at least one server; receiving, by the at least one server, the cargo transport sensor data from the network of multi-functional sensors; where the at least one server is configured to execute cargo quality shortfall administration software stored on a non-transient computer readable medium associated with the at least one server; dynamically predicting, by the at least one server, based at least in part on the cargo transport sensor data, at least one current quality metric of the transported cargo, where the at least one current quality metric is representative of a predicted quality loss of the transported cargo from an original condition of the transported cargo at the at least one first geographic location; dynamically determining, by the at least one server, based at least in part on the at least one current quality metric of the transported cargo and a cargo-specific value remaining curve of the quality determination, a current loss value of the transported cargo; dynamically determining, by the at least one server, based at least in part on cargo transport sensor data and prior to an arrival of the transported cargo to the at least one second geographic location, one or more remedial actions to mitigate the current loss value of the transported cargo or avoid an additional loss value of the transported cargo, where the one or more remedial actions include: 1) instantaneously instructing to pay, based on the quality determination, a payout amount to an owner of the transported cargo to compensate the current loss value of the transported cargo without a physical inspection of the transported cargo, and 2) transmitting the one or more remedial instructions, where the one or more remedial instructions includes at least one adjustment to one or more of: the at least one cargo container, the at least one cargo transport, and the at least one cargo storage, to remedy or prevent the additional loss value of the transport cargo.

In some embodiments and, optionally, in combination of any embodiment described above or below, the at least one environmental condition is one of: temperature, humidity, vibration, shock, sound, light, presence of air contaminant, pH, location, presence of at least one odor, presence of at least one gas, physical integrity of one of the transported item or the plurality of transported items, and any combination thereof.

In some embodiments and, optionally, in combination of any embodiment described above or below, the at least one server is further configured to calculate an insurance premium to be paid by the owner so that the owner is entitled to receive the payout amount.

In some embodiments and, optionally, in combination of any embodiment described above or below, the calculation of the insurance premium is based at least in part on at least one of: 1) historical quality data associated with one or more past cargo transportations of the transported cargo, or 2) one or more expert opinion associated with at least one of i) the quality loss of the transported cargo or ii) an operation of one or more of: the at least one cargo transport, the at least one cargo container, and the at least one cargo.

In some embodiments and, optionally, in combination of any embodiment described above or below, the at least one communication mode is one of, but not limited to: NFC, RFID, Narrow Band Internet of Things (NBIOT), ZigBee, 3G, 4G, 5G, GSM, GPRS, WiFi, WiMax, CDMA, satellite, and any combination thereof.

In some embodiments and, optionally, in combination of any embodiment described above or below, the executing at least one remedial activity comprises generating, in real-time, at least one alert configured to invoke at least one corrective action from the at least one transport.

In some embodiments and, optionally, in combination of any embodiment described above or below, the at least one corrective action is an instruction to change at least one transporting parameter.

In some embodiments and, optionally, in combination of any embodiment described above or below, wherein the at least one transporting parameter is an operational parameter of the at least one transport.

In some embodiments and, optionally, in combination of any embodiment described above or below, the at least one transporting parameter is a change in a transporting direction.

In some embodiments and, optionally, in combination of any embodiment described above or below, the execution of the at least one remedial activity comprises:
determining, based at least in part on the current quality metric, a current remaining economic value of one of the transported item or the plurality of transported items;
determining, based at least in part on the target quality metric, a target remaining economic value of one of the transported item or the plurality of transported items; and
determining a monetary shortfall loss amount representing a difference between the current remaining economic value and the target remaining economic value; and
causing to distribute the monetary shortfall loss amount to an owner of one of the transported item or the plurality of transported items.

In some embodiments and, optionally, in combination of any embodiment described above or below, the at least one server is further configured to calculate an insurance premium to be paid by the owner so that the owner is entitled to receive the monetary shortfall loss amount. In some embodiments and, optionally, in combination of any embodiment described above or below, the calculation of the insurance premium is based at least in part on at least one historical quality metric collected for previously transported items.

In some embodiments and, optionally, in combination of any embodiment described above or below, the at least one server having cargo quality shortfall administration software includes at least one machine learning algorithm configured to determine at least one of: i) the at least one current quality metric and ii) the at least one target quality metric. In some embodiments and, optionally, in combination of any embodiment described above or below, the at least one machine learning algorithm is neural network.

While a number of embodiments of the present disclosure have been described, it is understood that these embodiments are illustrative only, and not restrictive, and that many modifications may become apparent to those of ordinary skill in the art, including that the inventive methodologies, the inventive systems, and the inventive devices described herein can be utilized in any combination with each other. Further still, the various steps may be carried out in any desired order (and any desired steps may be added and/or any desired steps may be eliminated).

The invention claimed is:

1. A system comprising:
a network of multi-functional sensors associated with a cargo during a transport of the cargo;
   wherein the network of multi-functional sensors is associated with the cargo based at least in part on at least one quality metric that is utilized in determining a pre-determined quality score, indicative of an original condition of the cargo prior to the transport;
   wherein at least one multi-functional sensor of the network of multi-functional sensors is configured to measure, in real-time, at least one transport-related condition, at least one cargo-related condition, or both, to form cargo transport sensor data;
   wherein the at least one multi-functional sensor of the network of multi-functional sensors comprises a control board and a communication module, the communication module is configured to:
      receive, via one or more communication modes, at least one remedial instruction and
      communicate, via the one or more communication modes, at least one real-time adjustment to at least one other device;
      wherein the at least one real-time adjustment instructs at least one operational change in the at least one other device to cause at least one change to at least one operational parameter of one of a cargo container, the transport of the cargo, or the cargo, to maintain, based at least in part on at least one remedial action, the cargo at or above the pre-determined quality score indicative of the original condition of the cargo;
at least one server device having cargo quality administration software stored on a non-transient computer readable medium;
   wherein the at least one server device is remotely located from the network of multi-functional sensors;
   wherein, upon execution of the cargo quality administration software, the at least one server device is configured to:
   i) receive the cargo transport sensor data from the network of multi-functional sensors;
   ii) automatically and dynamically predict a current quality score of the cargo during the transport from the pre-determined quality score of the cargo, based at least in part on the cargo transport sensor data and at least one of:
      a) at least one item attribute of at least one item in the cargo, or
      b) at least one item characteristic category of the at least one item in the cargo; and
   iii) automatically and dynamically determine the at least one remedial action chosen from a plurality of remedial actions, pre-defined within cargo quality administration software, based at least in part on the current quality score of the cargo, the pre-determined quality score of the cargo, and a curve defining a relationship between the current quality score of the cargo and a percent remaining monetary value of the cargo;
   wherein the plurality of remedial actions comprises:
      a) compensating, in real-time, for a reduction in an initial monetary value of the cargo, and
      b) generating, in real-time, and communicating, to the at least one multi-functional sensor, via the one or more communication modes, the at least one remedial instruction that instructs the at least one multi-functional sensor to instruct the at least one operational change in the at least one other device to cause at least one change to at least one operational parameter of one of a cargo container, the transport of the cargo, or the cargo, to maintain the cargo at or above the pre-determined quality score of the cargo based at least in part on the at least one remedial action;
   wherein the at least one remedial action of compensating, in real-time, for the reduction in the initial monetary value of the cargo comprises:
      instantaneously instructing, during the transport of the cargo, to pay, without physical inspection of the cargo, a payout amount based at least in part on:
      1) The pre-determined quality score of the cargo,
      2) the current quality score of the cargo, and
      3) the curve.

2. The system of claim 1, wherein the at least one condition is one of:
   temperature, humidity, vibration, shock, sound, light, presence of air contaminant, pH, location, presence of at least one odor, presence of at least one gas, physical integrity of at least one item of the cargo, or any combination thereof.

3. The system of claim 1, wherein the one or more communication modes comprise: NFC, RFID, NBIOT, ZigBee, B3G, 4G, 5G, GSM, GPRS, WiFi, WiMax, CDMA, satellite, or any combination thereof.

4. The system of claim 1, wherein the at least one real-time adjustment is an instruction to replace one or more of: a current cargo transport, a current cargo container, or a current cargo storage, with one or more of: a new cargo transport, a new cargo container, or a new cargo storage, respectively.

5. The system of claim 1, wherein the one or more operational parameters of the at least one cargo transport comprise a speed of the at least one cargo transport and wherein the at least one operational change is a change in the speed of the at least one cargo transport.

6. The system of claim 1, wherein the one or more operational parameters of the at least one cargo transport comprise a geographic direction of the at least one cargo transport and wherein the at least one operational change is a change in the geographic direction of the at least one cargo transport.

7. The system of claim 1, wherein the at least one server and the network of multi-functional sensors are associated with distinct entities.

8. The system of claim 1, wherein the at least one server is further configured to calculate an insurance premium to be paid by an owner so that the owner is entitled to receive the payout amount.

9. The system of claim 8, wherein a calculation of the insurance premium is based at least in part on at least one of: 1) historical quality data associated with one or more past cargo transportations of other cargo of a type of the cargo, or 2) one or more expert opinion associated with at least one of i) the pre-determined quality score of the type of the cargo or ii) an operation of one or more of: the transport of the cargo, the cargo container, or the cargo.

10. The system of claim 1, wherein the at least one server having cargo quality shortfall administration software comprises at least one machine learning algorithm configured to dynamically predict the current quality score of the cargo.

11. The system of claim 10, wherein the at least one machine learning algorithm is a neural network.

12. A method comprising:
receiving, by at least one server, cargo transport sensor data of cargo from a network of multi-functional sensors during a transport of the cargo;
wherein the at least one server is remotely located from the network of multi-functional sensors;
wherein the network of multi-functional sensors is associated with the cargo based at least in part on at least one quality metric that is utilized in determining a pre-determined quality score indicative of an original condition of the cargo prior to the transport;
wherein at least one multi-functional sensor of the network of multi-functional sensors is configured to measure, in real-time, at least one transport-related condition, at least one cargo-related condition, or both, to form cargo transport sensor data;
wherein the at least one multi-functional sensor of the network of multi-functional sensors comprises a control board and a communication module, the communication module is configured to:
receive, via one or more communication modes, at least one remedial instruction and
communicate, via the one or more communication modes, at least one real-time adjustment to at least one other device;
wherein the at least one real-time adjustment instructs at least one operational change in the at least one other device to cause at least one change to at least one operational parameter of one of a cargo container, the transport of the cargo, or the cargo, to maintain, based at least in part on at least one remedial action, the cargo at or above the pre-determined quality score indicative of the original condition of the cargo;
automatically and dynamically predicting, by the at least one server, a current quality score of the cargo during the transport from the pre-determined quality score of the cargo, based at least in part on the cargo transport sensor data and at least one of:
a) at least one item attribute of at least one item in the cargo, or
b) at least one item characteristic category of the at least one item in the cargo; and automatically and dynamically determining, by the at least one server device, the at least one remedial action chosen from a plurality of remedial actions, pre-defined within cargo quality administration software, based at least in part on the current quality score of the cargo, the pre-determined quality score of the cargo, and a curve defining a relationship between the current quality score of the cargo and a percent remaining monetary value of the cargo;
wherein the plurality of remedial actions comprises:
a) compensating, in real-time, for a reduction in an initial monetary value of the cargo, and
b) generating, in real-time, and communicating, to the at least one multi-functional sensor, via the one or more communication modes, the at least one remedial instruction that instructs the at least one multi-functional sensor to instruct the at least one operational change in the at least one other device to cause at least one change to at least one operational parameter of one of a cargo container, the transport of the cargo, or the cargo, to maintain the cargo at or above the pre-determined quality score of the cargo based at least in part on the at least one remedial action;
wherein the at least one remedial action of compensating, in real-time, for the reduction in the initial monetary value of the cargo comprises:
instantaneously instructing, during the transport of the cargo, to pay, without physical inspection of the cargo, a payout amount based at least in part on:
1) The pre-determined quality score of the cargo,
2) the current quality score of the cargo, and
3) the curve.

13. The method of claim 12, wherein the at least one condition is one of:
temperature, humidity, vibration, shock, sound, light, presence of air contaminant, pH, location, presence of at least one odor, presence of at least one gas, physical integrity of at least one item of the cargo, or any combination thereof.

14. The method of claim 12, wherein the one or more communication modes comprise: NFC, RFID, NBIOT, ZigBee, B3G, 4G, 5G, GSM, GPRS, WiFi, WiMax, CDMA, satellite, or any combination thereof.

15. The method of claim 12, wherein the at least one real-time adjustment is an instruction to replace one or more of: a current cargo transport, a current cargo container, or a current cargo storage, with one or more of: a new cargo transport, a new cargo container, or a new cargo storage, respectively.

16. The method of claim 12, wherein the one or more operational parameters of the at least one cargo transport comprise a speed of the at least one cargo transport and wherein the at least one operational change is a change in the speed of the at least one cargo transport.

17. The method of claim 12, wherein the one or more operational parameters of the at least one cargo transport comprise a geographic direction of the at least one cargo transport and wherein the at least one operational change is a change in the geographic direction of the at least one cargo transport.

18. The method of claim 12, wherein the at least one server and the network of multi-functional sensors are associated with distinct entities.

19. The method of claim 12, wherein the at least one server is further configured to calculate an insurance premium to be paid by an owner so that the owner is entitled to receive the payout amount.

20. The method of claim 19, wherein a calculation of the insurance premium is based at least in part on at least one of: 1) historical quality data associated with one or more past cargo transportations of other cargo of a type of the cargo, or 2) one or more expert opinion associated with at least one of i) the pre-determined quality score of the type of the cargo or ii) an operation of one or more of: the transport of the cargo, the cargo container, or the cargo.

21. The method of claim 12, wherein the at least one server having cargo quality shortfall administration software comprises at least one machine learning algorithm configured to dynamically predict the current quality score of the cargo.

22. The method of claim 21, wherein the at least one machine learning algorithm is a neural network.

* * * * *